US012042426B2

(12) United States Patent
Breiter

(10) Patent No.: US 12,042,426 B2
(45) Date of Patent: Jul. 23, 2024

(54) HOT AND/OR COLD PAD

(71) Applicant: CALOPAD AG, Sempach Station (CH)

(72) Inventor: Michael Breiter, Sempach (CH)

(73) Assignee: CALOPAD AG, Sempach Station (CH)

(*) Notice: Subject to any disclaimer, the term of this patent is extended or adjusted under 35 U.S.C. 154(b) by 482 days.

(21) Appl. No.: 16/965,620

(22) PCT Filed: Jan. 28, 2019

(86) PCT No.: PCT/IB2019/050659
§ 371 (c)(1),
(2) Date: Jul. 29, 2020

(87) PCT Pub. No.: WO2019/150238
PCT Pub. Date: Aug. 8, 2019

(65) Prior Publication Data
US 2021/0052418 A1 Feb. 25, 2021

(30) Foreign Application Priority Data

Jan. 30, 2018 (EP) .................................... 18154286
Jan. 30, 2018 (WO) .................. PCT/IB2019/000093

(51) Int. Cl.
A61F 7/02 (2006.01)
A61F 7/00 (2006.01)
(Continued)

(52) U.S. Cl.
CPC ............... A61F 7/02 (2013.01); A61F 7/007 (2013.01); A61B 5/0531 (2013.01);
(Continued)

(58) Field of Classification Search
CPC ....... A61B 5/4836; A61B 5/4561; A61B 5/45; A61B 5/0531; A61B 5/1116; A61B 5/389;
(Continued)

(56) References Cited

U.S. PATENT DOCUMENTS 2,198,989 A * 4/1940 Cooley .................. A61F 7/007
219/528
8,658,943 B1 2/2014 Larsen
(Continued)

FOREIGN PATENT DOCUMENTS

DE 102012203880 A1 9/2013
EP 3217761 A1 9/2017
(Continued)

Primary Examiner — Joanne M Rodden
Assistant Examiner — Matthew David Becton
(74) Attorney, Agent, or Firm — HULTQUIST, PLLC; Steven J. Hultquist

(57) ABSTRACT

The invention relates to a heating and/or cooling device (10) for delivering heating and/or cooling energy to the body of a living being (28). The heating and/or cooling device (10) comprises a heating and/or cooling pad (12) which can be connected to the body of the person (28). The heating and/or cooling pad has an upper face (122) and a lower face (121), and an adhesive surface (1210) is provided on the lower face (121) for attaching the heating and/or cooling pad (12) to the surface of the skin of the person (28). The heating and/or cooling pad comprises at least one heating and/or cooling element (26) by means of which electrical energy output by an electrical energy source (22) can be converted into heating and/or cooling energy. The heating and/or cooling device (10) further comprises a control unit (14) which is provided for fixedly or detachably accommodating the energy source (22) and has a signal processor (16). Furthermore, the control unit (14) is provided for outputting an open-loop and/or closed-loop control signal, by means of which the energy output from the energy source (22) to the heating and/or cooling element (26) can be controlled. The heating and/or cooling pad (12) and the control unit (14) can be electrically and mechanically connected to one another by at least one electrical connector (18a, 18b), via which the electrical energy can be transmitted to the heating and/or (Continued)

cooling element (26), and by at least one mechanical and/or magnetic connector (20a, 20b).

11 Claims, 6 Drawing Sheets

(51) Int. Cl.
| | |
|---|---|
| A61B 5/00 | (2006.01) |
| A61B 5/0531 | (2021.01) |
| A61B 5/11 | (2006.01) |
| A61B 5/389 | (2021.01) |

(52) U.S. Cl.
CPC ............ *A61B 5/1116* (2013.01); *A61B 5/389* (2021.01); *A61B 5/4836* (2013.01); *A61B 5/6833* (2013.01); *A61F 2007/0071* (2013.01); *A61F 2007/0075* (2013.01); *A61F 2007/0078* (2013.01); *A61F 2007/0093* (2013.01); *A61F 2007/0096* (2013.01); *A61F 2007/0226* (2013.01)

(58) Field of Classification Search
CPC ........... A61B 5/6833; A61F 2007/0093; A61F 2007/0096; A61F 7/02; A61F 7/007; A61F 2007/0226

See application file for complete search history.

(56) References Cited

U.S. PATENT DOCUMENTS

| | | | |
|---|---|---|---|
| 2015/0297445 A1 | 10/2015 | Gordon | |
| 2015/0335288 A1* | 11/2015 | Toth | ..................... A61B 5/6833 |
| | | | 600/391 |
| 2016/0331959 A1 | 12/2016 | Hsieh | |
| 2017/0209301 A1* | 7/2017 | DeSeve | .................. A41D 1/005 |
| 2018/0193185 A1* | 7/2018 | Thomas | .................. A61F 7/007 |
| 2018/0214304 A1* | 8/2018 | Atkinson | .................. A61F 7/12 |

FOREIGN PATENT DOCUMENTS

| | | | | |
|---|---|---|---|---|
| KR | 20150083559 A | | 7/2015 | |
| NO | 20151454 A1 | * | 4/2017 | ......... A61N 1/36021 |
| WO | 2017074196 A1 | | 5/2017 | |

* cited by examiner

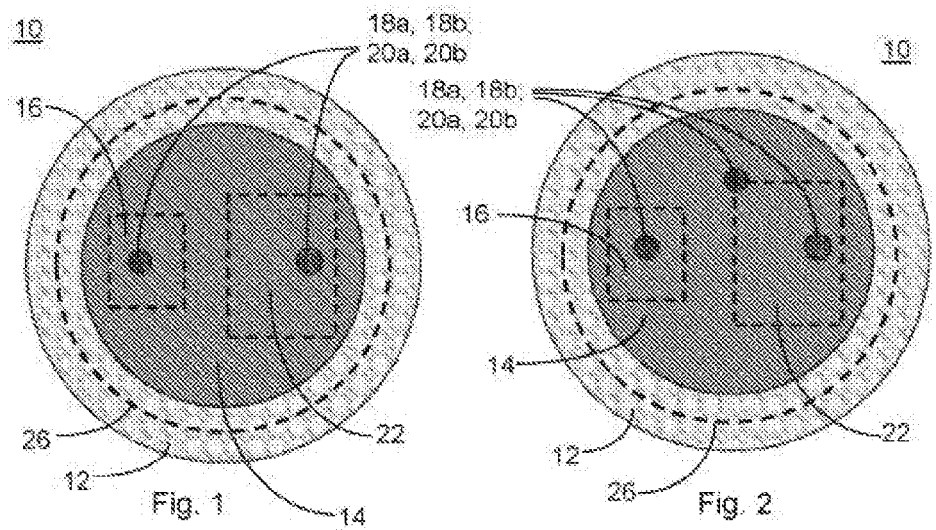
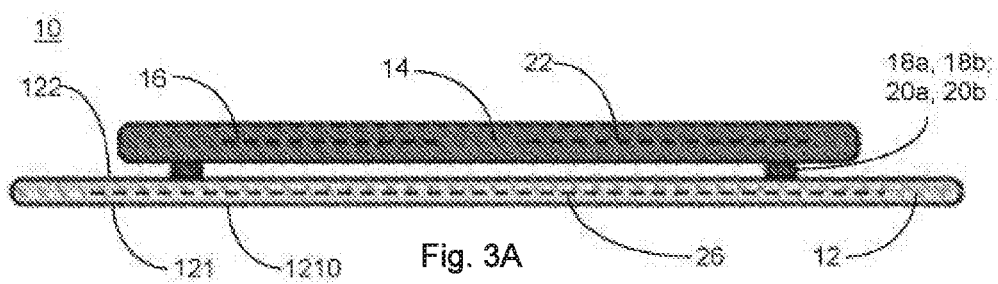
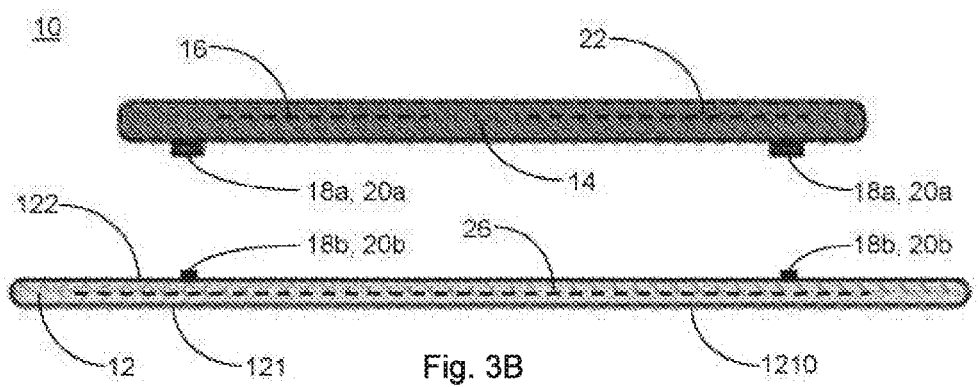

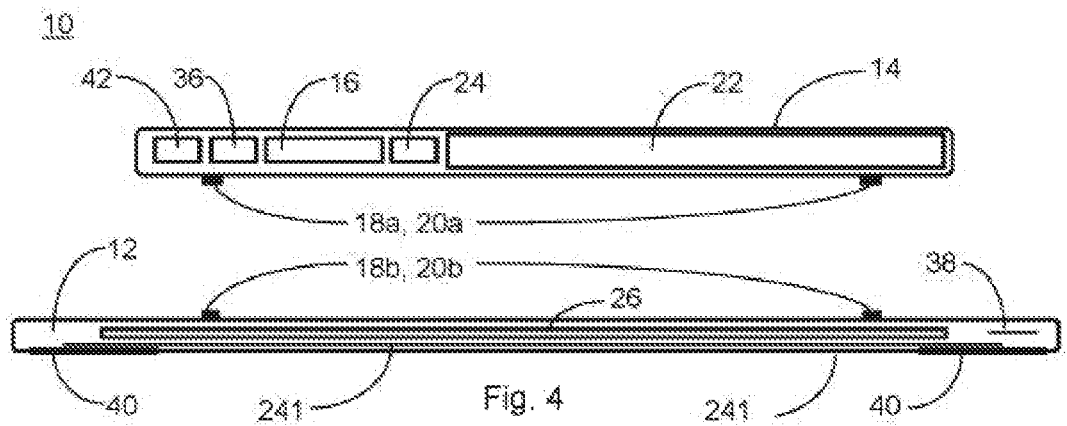
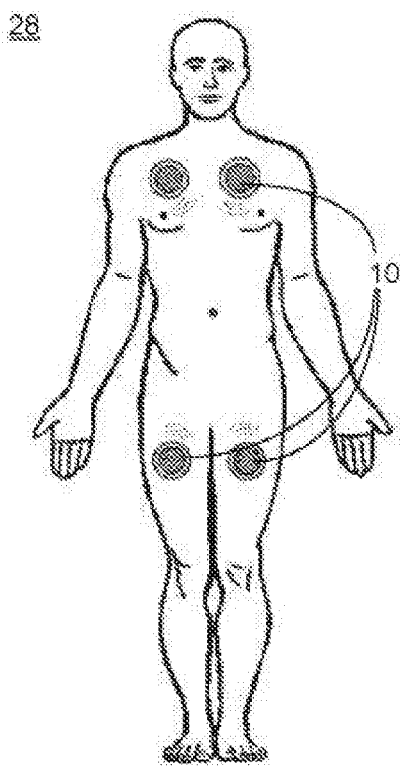
Fig. 5A
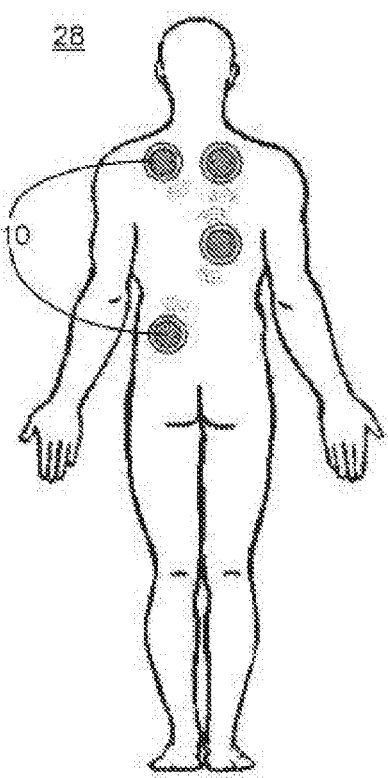
Fig. 5B

HOT AND/OR COLD PAD

CROSS REFERENCE TO RELATED APPLICATIONS

This application is the U.S. national stage of International Application No. PCT/IB2019/050659, filed on 2019 Jan. 28. The international application claims the priority of EP 18154286.1 filed on 2018 Jan. 30; all applications are incorporated by reference herein in their entirety.

BACKGROUND

Technical Field

The present invention relates to a heating and/or cooling device for delivering heating and/or cooling energy to the body and to a method for open-loop and/or closed-loop control of such a device, as well as to a computer program having a program code for carrying out the method.

Prior Art

The majority of the population suffers from sometimes "chronic" neck and back tension. Chronic neck and back tension can lead to incorrect posture. Tension and bad posture can result in poor blood circulation in the muscles, which can promote migraines, for example. Moreover, in the event of neck and back tension, a relieving posture is often adopted in order to avoid pain. A prolonged relieving posture can cause enormous damage to joints. In addition, the intervertebral disks can wear out due to poor posture, which can lead to an acute herniated disk. This has in particular long-term consequences. Many affected people try to remove the tension or pain using passive means such as ointments or heat plasters, without any additional effort or movement. Often, pain remains and can become chronic.

From the prior art, heat plasters, for example, are known for the treatment of pain, in particular neck and back tension, as mentioned above. These heat plasters can generate heat by means of a chemical reaction. However, these heat plasters can also cause skin rashes in many patients due to the chemical reaction that generates the heat. In addition, heat plasters containing chemical reaction agents must be replaced regularly with new heat plasters. This is not sustainable.

Moreover, a heat plaster cannot generate a constant heat at the painful or tense point over a longer period of time. The pain is therefore relieved only for a short period of time and in particular a longer-lasting treatment is expensive. The heat is also generated only on the surface of the skin and does not penetrate deeper into the body. A deep warmth therefore cannot be generated.

Furthermore, it is not possible to regulate the temperature, which, depending on the person and the skin type, can cause skin injuries such as redness or burns if too much heat is applied.

The heat supply also cannot be switched on and off. An alternating supply of heat (switching on/off) is not possible with conventional heat plasters. Furthermore, traditional heat plasters require approximately >30 minutes until the therapeutic heat of 42° C. is reached. A continuous supply of heat can have a negative influence on the healing process, depending on the ailment. A continuous supply of heat can lead to the muscle tissue becoming accustomed to the heat, as a result of which there is no relaxing effect. It is therefore not possible to use intelligent heat therapy methods, as the heat is released in an uncontrolled manner.

There is also the risk of incorrect application of heat therapy. Heat patches are often applied only to the place where the pain occurs or has been localized. This can relieve the pain and tension in the short term, but new tension can arise in other parts of the body, as the warming place is relieved while other places become cramped as a result. This can cause further tension due to the incorrect application of local heat.

Larger heating pads are also known, which can be directly connected to the power supply via a socket. These heating pads are relatively inflexible and, as the power cable has to be connected to a socket, they greatly restrict freedom of movement in everyday life.

SUMMARY

The invention relates to a heating and/or cooling device (10) for delivering heating and/or cooling energy to the body of a living being (28). The heating and/or cooling device (10) comprises a heating and/or cooling pad (12) which can be connected to the body of the person (28). The heating and/or cooling pad has an upper face (122) and a lower face (121), and an adhesive surface (1210) is provided on the lower face (121) for attaching the heating and/or cooling pad (12) to the surface of the skin of the person (28). The heating and/or cooling pad comprises at least one heating and/or cooling element (26) by means of which electrical energy output by an electrical energy source (22) can be converted into heating and/or cooling energy. The heating and/or cooling device (10) further comprises a control unit (14) which is provided for fixedly or detachably accommodating the energy source (22) and has a signal processor (16). Furthermore, the control unit (14) is provided for outputting an open-loop and/or closed-loop control signal, by means of which the energy output from the energy source (22) to the heating and/or cooling element (26) can be controlled. The heating and/or cooling pad (12) and the control unit (14) can be electrically and mechanically connected to one another by at least one electrical connector (18a, 18b), via which the electrical energy can be transmitted to the heating and/or cooling element (26), and by at least one mechanical and/or magnetic connector (20a, 20b).

DETAILED DESCRIPTION

Object of the Invention

The object of the present invention is to provide an improved concept for the delivery of heating and/or cooling energy to the body of a living being and/or an animal (hereinafter referred to as living being) which is more cost-effective, more sustainable and more intelligent.

Achieving the Object

This object is achieved by the device according to the invention according to claim 1, the method according to the invention according to claim 14, and the computer program according to the invention according to claim 16.

Detailed Description

Embodiments of the present invention comprise a heating and/or cooling device for the delivery of heating and/or cooling energy to the body of a living being. The heating and/or cooling device comprises a heating and/or cooling pad which can be connected to the body of the living being. The heating and/or cooling pad has an upper face and a lower face, an adhesive surface being provided on the lower face thereof for securing the heating and/or cooling pad to the surface of the skin of the living being. The heating and/or cooling pad comprises at least one heating and/or cooling element, by means of which electrical energy output from an electrical energy source can be converted into heating and/or cooling energy. The heating and/or cooling device additionally comprises a control unit which is provided to rigidly or releasably receive the energy source and has a signal processor. Furthermore, the control unit is provided for outputting an open-loop and/or closed-loop control signal, by means of which the output of energy from the energy source to the heating and/or cooling element can be controlled in an open-loop and/or closed-loop manner. The heating and/or cooling pad and the control unit can be electrically and mechanically connected to one another by means of at least one electrical connecting element, via which the electrical energy can be transmitted to the heating and/or cooling element, and by at least one mechanical and/or one magnetic connector.

Embodiments provide concepts for delivering heating and/or cooling energy to the body of a living being. The heating and/or cooling pad can be arranged, stuck or attached to the body of a living being by means of an adhesive surface. The heating and/or cooling pad can have a more or less flat shape or be designed so as to be flat, such that, as far as possible, no pressure points are created on the body of the living being when the heating and/or cooling device is worn. Furthermore, the heating and/or cooling pad is flexible due having as flat a shape as possible. The heating and/or cooling pad may have a substantially flat shape with a lower face or a first surface and an upper face or a second surface. The adhesive surface may be provided or formed on the lower face of the heating and/or cooling pad. The adhesive surface may be provided with a protective layer to prevent accidental attachment, which may be removed before attachment to the body. The heating and/or cooling pad can absorb electrical energy or electric current and convert it into heating and/or cooling energy or thermal energy, for example. This conversion can take place, for example, by means of an electrical resistor or an electrical warming or heating and/or cooling element. The electrical resistor or the electrical heating and/or cooling element can convert electrical energy into heat. The heat and/or cold can be delivered to the body of the living being by the contact of the heating and/or cooling pad with the body of the living being.

The muscle or muscles located under the skin at the site of the heating and/or cooling pad that delivers heat and/or cold to the body can be stimulated by the heat and/or cold delivered to the body by the heating and/or cooling pad. The delivery of heat and/or cold to muscles and other soft tissue can relax tightened or contracted muscles and/or soft tissue. In addition, the delivery of heat and/or cold to muscles can stimulate the blood circulation of the muscle.

By stimulating the muscles, cramps can be relieved and pain can be reduced. It is also possible that the antagonist of a muscle or group of muscles is stimulated to relax the cramped opposing part(s). As a result of the relaxed muscles and the relaxed musculature in general, the posture and/or movement of the living being improves. "Posture," which can be understood statically, also always refers in the following to a body movement, which can be understood dynamically. A good posture can protect joints and reduce pain, thus increasing the well-being of the living being.

By using an electrical energy storage device instead of a chemical energy storage device, such as a heat plaster, there is no danger of allergic skin reactions to the chemical energy storage device.

The heating and/or cooling device can also comprise the control unit, on which a signal processor, a processor unit or a controller can be arranged. The signal processor can be designed to generate an open-loop and/or closed-loop control signal or a signal for open-loop and/or closed-loop control of an electrical energy source. The signal processor can receive and process data or signals and transmit data or signals. The signals can be received or transmitted as radio signals or wired signals, analog or digital signals. The data can, for example, be generated by sensors or a controller and fed to the signal processor. The processing can be carried out by evaluating or assessing or comparing the measured or acquired data with reference data, for example. The processing can be carried out by software or hardware.

The signal processor can be designed to control the flow of energy from an electrical energy source. The signal processor can also be designed to control the thermal energy supply or energy delivery to the body or muscles. The electrical energy can be delivered continuously, for example, from the electrical energy source to the heating and/or cooling pad by adjusting the power or by changing a pulse-pause ratio.

The electrical energy source can be e.g. a battery or an accumulator. The battery or accumulator can emit electrical energy or electric current. An accumulator can be charged or recharged with electrical energy via a further energy source and a charging circuit.

An accumulator or battery, for example, as a mobile electrical energy source can thus provide the electrical energy for the heating and/or cooling pad. In addition, the electrical energy source can supply electrical energy to the signal processor, sensors, radio unit, vibration generator, electrodes, heating element, or transmission units. The battery or accumulator may be attached or attachable to the control unit. However, the electrical energy can also be transmitted to the control unit via a cable, for example. The cable can be connected to a power supply unit or a socket that provides the energy. The energy source, which can be detachably accommodated in the control unit, can therefore also be an external energy source, which is accommodated in the control unit via a cable, e.g. a power cable.

The electric current can be transferred from the control unit or the electrical energy source to the heating and/or cooling pad via an electrical connector or an electrical connecting element. The electrical connector allows electrical coupling and separation between the control unit or electrical power source and the heating and/or cooling pad. Complementary electrical connecting elements such as a plug or pin and a matching socket or magnets or push buttons can be used to create a safe and reliable electrical connection that can be disconnected. Complementary connecting elements are connecting elements which create a non-positive and/or positive connection to each other.

In addition, at least one mechanical and/or magnetic connector or a mechanical and/or magnetic connecting element can be arranged on the control unit and a complementary mechanical and/or magnetic connecting element on the heating and/or cooling pad. The connecting element can be arranged on the upper face of the heating and/or cooling pad or on the surface of the heating and/or cooling pad opposite the adhesive surface. This allows the heating and/or cooling pad to be arranged between the control unit and the body of the living being. A safe and reliable mechanical and/or magnetic coupling between the control unit and the heating and/or cooling pad can be established by means of the mechanical and/or non-mechanical connector, which coupling can be separated. Complementary mechanical and/or magnetic connecting elements, such as those mentioned above for the electrical connecting elements, can be used to create a safe and reliable mechanical and/or magnetic connection which can be separated. The mechanical and/or magnetic connecting elements allow the heating and/or cooling pad to be separated from the control unit after use for cleaning or disposal. The control unit can be reused as often as required, thus reducing the maintenance or operating costs of the heating and/or cooling device and providing a sustainable benefit.

In a preferred embodiment, the electrical connector has a first electrical connecting element connected to the control unit and a second connecting element connected to the heating and/or cooling pad. The mechanical and/or magnetic connector comprises a first mechanical and/or magnetic connecting element connected to the control unit and a second mechanical and/or magnetic connecting element connected to the heating and/or cooling pad. The first and second mechanical connecting elements each enclose the corresponding first and second electrical connecting elements. The electrical connector or the electrical connecting element or the electrical interface can be arranged or integrated in the mechanical connector or the mechanical connecting element. The mechanical and/or magnetic connector or the mechanical and/or magnetic connecting element may also be arranged or integrated in the electrical connector or the electrical connecting element. This has the advantage that fewer connectors need to be connected or coupled to one another when connecting the heating and/or cooling pad to the control unit. This simplifies operation and handling. Metal push buttons, magnets or a click system, for example, can be used as connecting elements. On the one hand, the connection system should provide a mechanically stable, detachable connection, and on the other hand, the electrical resistance should be as low as possible.

In a particularly preferred embodiment, at least three mechanical and/or magnetic connecting elements are formed on the control unit and three complementary mechanical and/or magnetic connecting elements are formed opposite each other on the heating and/or cooling pad at the same location. A stable mechanical and/or magnetic connection between the heating and/or cooling pad and the control unit can be established by three mechanical and/or non-mechanical connecting elements. This is in particular the case when the heating and/or cooling device is attached to the body of a living being. If there are more than two mechanical and/or magnetic connecting elements, the position of the connecting elements when attaching the heating and/or cooling device to the body of the living being is less important. In addition, three or more connecting elements can be used, especially if the connecting elements are arranged asymmetrically, to provide a position-optimized or position-determined connection between the heating and/or cooling pad and the control unit. This means that the control unit can be connected to the heating and/or cooling pad in two positions (0° and/or 180°). Malfunctions or short circuits between the control unit and the heating and/or cooling pad are not possible.

In a preferred embodiment, the energy source and the heating and/or cooling element is designed to heat and/or cool the heating and/or cooling pad by 20 K in less than 1 minute, preferably in less than 20 seconds, particularly preferably in less than 5 seconds. This offers the advantage that the body can be quickly supplied with heating and/or cooling energy, e.g. at trigger points of the muscles, due to the rapid heating and/or cooling. This can lead to particularly effective stimulation of the muscles and thus relaxation of the muscles. The heating and/or cooling pad can be quickly heated and/or cooled from 8° to 42° C., preferably also up to 45° C. and vice versa (therapeutic heat and/or cold). The body reacts very sensitively to heat and/or cold in the range of its own body temperature (36° C.) and temperature changes in this range are clearly perceived.

In a particularly preferred embodiment, the heating and/or cooling device comprises at least one posture sensor. The posture sensor can be designed to detect the posture and/or movement of the living being at least in part. The posture sensor can generate posture data. The posture sensor can be arranged or formed on the control unit. The posture sensor can comprise at least one of the following sensors, e.g. a 3D gyro sensor, an acceleration sensor, a bending sensor, a temperature sensor or a sensor with strain gauges. The posture data output by the posture sensor(s) can be used to determine the posture or movement. The posture data can be fed or transmitted to the signal processor.

By means of a posture sensor or the posture data generated, it is possible to recognize or determine whether the posture of the living being is correct or whether the posture is incorrect or poor. It is also possible to detect only part of the posture, e.g. the posture of the upper body of a living being, by means of at least one posture sensor and to generate posture data.

Correct posture can include relaxed muscles. Correct posture can include the entire body being upright. With correct posture, the body should not lean against the left-hand or right-hand side of the body. The head or body may appear to be attached to or suspended from an invisible thread that exits at the highest point of the head when the posture is correct. If the posture is wrong or poor, the body may tilt too far forward, backward, left or right. It is also possible that the shoulders, for example, are pulled up or down too much. Furthermore, a hump or a hollow back can be poor or wrong posture. Correct posture is an indication of relaxed muscles. Incorrect posture is an indication of tense or cramped muscles.

Relaxed posture can be different. Certain living beings can have, for example, congenital postures or postures that have changed due to illness, accident or age. It is also possible to define this changed posture as correct posture and to consider deviations from this changed posture as a posture fault or incorrect posture. It is also possible, for example, to calibrate the current posture or correct posture so that living beings with, for example, congenital posture disorders do not display any false posture data.

The posture can be determined by evaluating or assessing the posture data or comparing the measured or recorded posture data with reference posture data in the signal processor. By determining the posture, it can be recognized whether, for example, tension is present in the body or in the muscles of the living being. Muscle tensions can cause pain in various parts of the body, such as the neck or back. The posture data can show exactly where the problem needs to be tackled or solved.

If it is recognized on the basis of posture that a certain muscle or several muscles are tense, these muscles can be stimulated or relaxed by supplying energy or heat and/or cold, for example. Depending on the body data, the signal processor can change the signal by means of which the energy output from the energy source to the heating and/or cooling element can be controlled.

In another preferred embodiment, the heating and/or cooling device comprises a radio unit for transmitting and/or receiving data. The data may include sensor data, control data, status data or other data. The radio unit can be arranged or formed on the control unit. By means of the radio unit, a first heating and/or cooling device can exchange data with at least one second heating and/or cooling device. However, the radio unit also allows the heating and/or cooling device to exchange data with a mobile device such as a tablet, a mobile telephone or a smartphone. The data can be exchanged between the signal processor on the first heating and/or cooling device and a signal processor on the second heating and/or cooling device or a signal processor on a mobile device. This can, for example, increase user-friendliness in control and efficiency in treatment.

In a preferred embodiment, the heating and/or cooling device comprises a temperature sensor which is designed to generate temperature data and the signal processor is designed to generate the open-loop and/or closed-loop control signal for open-loop and/or closed-loop control of the electrical energy source depending on the temperature data. The temperature sensor can be arranged on the heating and/or cooling device, for example on the heating and/or cooling pad. The temperature sensor can detect or measure the surface temperature of the skin and/or the temperature of the heating and/or cooling pad. A plurality of temperature sensors can also be arranged on the heating and/or cooling device or the heating and/or cooling pad. Depending on the detected temperature of the temperature sensor, the open-loop and/or closed-loop control signal for open-loop and/or closed-loop control of the electrical energy source and/or the electric current can be generated. The signal processor, for example, can be designed to generate the open-loop and/or closed-loop control signal for open-loop and/or closed-loop control of the electric current depending on the temperature data or the detected temperature and thus for open-loop and/or closed-loop control of the output of the heating and/or cooling energy or the temperature of the heating and/or cooling pad. The temperature of the heating and/or cooling pad can therefore be controlled in an open-loop or closed-loop manner.

Measuring the body temperature or the surface temperature of the skin can provide the living being with a pleasant, warm and/or cool body feeling, for example. Furthermore, the temperature of the heating and/or cooling pad can be adjusted to the optimal treatment temperature. Furthermore, this can prevent that burns or other skin injuries being caused by excessive heating and/or cooling of the heating and/or cooling pad.

Depending on the living being and the skin type, different high and/or low temperatures on the heating and/or cooling pad can be perceived as pleasant and cause stimulation or healing of the muscle. If the heating and/or cooling pad is not heated and/or cooled sufficiently, the muscle is not stimulated or is not relaxed and therefore there is no positive effect for the living being, as the pain is not alleviated, for example. By detecting or measuring the temperature of the heating and/or cooling pad and comparing it with a target value or a target temperature, an optimal temperature can be generated on the heating and/or cooling pad. If the temperature sensor measures a temperature on the skin that is lower than a target temperature, the heating and/or cooling pad can be activated by the signal processor, for example, and convert electrical energy into heating and/or cooling energy. By delivering the heating and/or cooling energy to the skin, the skin can be heated and/or cooled down to a predetermined target temperature. Once the target temperature is reached, the conversion of the heating and/or cooling energy in the heating and/or cooling pad is reduced or increased until the temperature of the skin drops below or above a predetermined value again.

The temperature is preferably detected on the surface of the heating and/or cooling pad that is in contact with the skin (adhesive surface). The electric current is controlled correspondingly depending on the temperature of the heating and/or cooling pad. If the target temperature of the heating and/or cooling pad is higher than the measured temperature, the electric current or the delivery of electrical energy to the heating and/or cooling pad can be increased. If the target temperature of the heating and/or cooling pad is lower than the measured temperature, the electric current or the delivery of electrical energy to the heating and/or cooling pad can be reduced. In this way a predetermined or optimum temperature can be achieved on the adhesive surface of the heating and/or cooling pad. The heat delivery can be constant over the entire surface or adhesive surface or film surface of the heating and/or cooling pad.

Experiments have shown that the temperature of the heating and/or cooling pad when in contact with the skin should be <60° C., preferably <50° C., particularly preferably <45° C. or in a range between 38° C. and 42° C. in the case of heating, in order to avoid skin injuries. Similarly, when cooling, the temperature should be in a range between 8° C. and 15° C. In particular in the case of small children, for example, the temperature should be <40° C. but above 8° C. to avoid skin injuries. In order to achieve muscle stimulation, the temperature should be >35° C., preferably >40° C., particularly preferably >45° C.

Furthermore, well-being regarding the temperature of a heating and/or cooling pad may depend on the size of said pad. The larger the heating and/or cooling pad, the lower the temperature at which it is operated, since the risk of skin injuries is greater with large heating and/or cooling pads. In addition, there is a risk that the body of the living being will overheat and/or overcool if large heating and/or cooling pads are used.

In another preferred embodiment, electrodes are arranged on the lower face of the heating and/or cooling pad and the signal processor is designed to determine muscle tension by electromyography and/or skin resistance by measuring the conductance of the skin. The heating and/or cooling device can comprise electromyography electrodes for measuring muscle tension. The electrodes for measuring muscle tension EMG can be arranged on the heating and/or cooling device. Electromyography (EMG) is used to measure electrical muscle activity. Electrodes placed on the surface of the skin can be used to measure potential changes in one or more muscles. The measurement of potential changes by means of EMG provides information about the muscle tension. The information about the muscle tension can be provided to the signal processor. The signal processor can be designed to generate a control signal adjusted to the muscle tension for controlling the electrical energy source. The information about the muscle tension can be used to achieve targeted relaxation by supplying heat to the muscles. Tensions in the musculature can thus be determined and eliminated. EMG sensors can also identify or record skin data. Other sensors for detecting muscle tension may be posture sensors such as a 3D gyro sensor (Gyroscope 3D), an acceleration sensor, a temperature sensor, a bending sensor or a strain gauge.

The heating and/or cooling device can comprise electrodes for detecting skin resistance. The heating and/or cooling device can comprise a skin resistance sensor which is designed to detect the skin resistance of the person. The signal processor can be designed to generate a control signal adjusted to the skin resistance for controlling the electrical energy source or for controlling the energy output from the energy source to the heating element. Detecting the skin resistance can determine, for example, how much the person is sweating. The heating and/or cooling device can also comprise a sensor for detecting moisture or skin moisture. Such moisture sensors change, for example, their electrical resistance depending on the moisture to be measured. The output of electrical energy by the electrical energy source and thus the heat delivery from the heating and/or cooling device can thus be controlled or changed depending on the skin resistance or the intensity of perspiration or transpiration of a living being.

In order to determine the skin resistance, the impedance between two electrodes that are in contact with the body can also be measured. The impedance also depends on the sweat on the surface of the skin. The signal processor can be designed to determine or measure the impedance. The signal processor can be designed to generate a control signal adjusted to the impedance for controlling the energy output from the energy source to the heating and/or cooling element.

In another preferred embodiment, the adhesive surface of the heating and/or cooling pad comprises an adhesive and/or a bonding element. A pressure-sensitive adhesive offers the advantage that the adhesive does not have a solidifying mechanism, which means that the adhesive does not form a permanent bond. This means that the heating and/or cooling pad can be detached from the surface of the user's body or skin after use and reattached to the body of a living being if necessary.

In a preferred embodiment, the adhesive is gel-like. The adhesive on the adhesive surface of the heating and/or cooling pad may comprise a gel-like adhesive or the consistency of the adhesive may be gel-like. Gel-like substances can adapt well to uneven surfaces such as the surface of the skin and can be in contact therewith over a large area. By being in contact with large areas, the heating and/or cooling energy can be easily transferred from the heating and/or cooling pad to the body of a living being.

In another preferred embodiment, the heating and/or cooling pad is a disposable element and the control unit is a reusable element. The heating and/or cooling pad can be stuck to the person's body or skin. For reasons of hygiene (sweat, body fat) or, for example, because different people use the heating and/or cooling device or because the adhesive effect of the adhesive wears off after a certain time, the heating and/or cooling pad can be disposed of after a certain period of use or after a certain number of uses.

The control unit can comprise the electronics or various electronic elements, which can be reused as required. The heating and/or cooling pad can be removed from the control unit after wearing out and replaced by a new heating and/or cooling pad. By reusing the control unit and only replacing the heating and/or cooling pad that comes into contact with the skin of the living being, the operating costs of the heating and/or cooling device can be reduced.

In another preferred embodiment, the heating and/or cooling device comprises a vibration generator which is designed to convert electrical energy emitted by the electrical energy source into mechanical energy which can be transmitted to the body of the person. The vibration generator can convert the electrical energy into mechanical energy and deliver it to the body in the form of vibrations, for example. The vibration generator can, for example, have an electric motor with an asymmetrically placed mass (imbalance) on the shaft. When the shaft of the electric motor is driven by the electrical energy, the mass connected to the shaft starts to rotate. The rotating mass creates an imbalance, which causes mechanical vibrations or mechanical energy. The imbalance is created by the offset of the shear point of the mass with respect to the rotational axis of the shaft. By contact of the heating and/or cooling device with the body of the living being, the mechanical energy can be transferred to the skin or body of the living being.

The mechanical energy is, inter alia, dependent on the mass or imbalance and the speed of rotation of the electric motor or the shaft of the electric motor. The greater the imbalance, the more mechanical energy is generated. In addition, the greater the speed of rotation of the mass or shaft of the electric motor, the greater the mechanical energy generated.

By transmitting the mechanical energy to the body of the living being, the person can perceive vibrations. These vibrations can inform the living being about incorrect posture or signal the incorrect posture. Due to the vibration, the living being can become aware and can, for example, improve its posture through its own conscious observation. Poor postures can thus be signaled by vibrations. The poor posture can also be signaled, for example, by a heating and/or cooling device close to the poor posture. In addition, the living being can also be informed about incorrect posture or improvements in posture by the output of information from the heating and/or cooling device to the living being, for example on the display of a mobile device. By means of the vibration, the living being can also be reminded, for example, of physical exercises (gymnastic exercises) for improving posture.

Furthermore, embodiments create a system for delivering heating and/or cooling energy to the body of a living being. The system can promote the relaxation of the body muscles. The system comprises at least one first heating and/or cooling device according to the described embodiments and at least one second heating and/or cooling device according to the described embodiments and/or a mobile device which is suitable for exchanging data with the first heating and/or cooling device. In embodiments, the system may be designed to transmit and/or receive data from the first heating and/or cooling device to the second heating and/or cooling device. The heating and/or cooling devices can thus exchange data with one another and form a network. The heating and/or cooling devices can also be designed to send data to and/or receive data from a mobile device. The mobile device may be a mobile telephone or smartphone or tablet or a mobile device specially designed to deliver heating and/or cooling energy to the body of a living being. A network can thus also be formed. The data can be sensor data, posture data, control data or other data that are essential for the operation of the heating and/or cooling devices. The heating and/or cooling devices can also be connected to one another via a cable.

Furthermore, a method is provided for controlling a heating and/or cooling device according to embodiments, which method is intended to deliver heating and/or cooling energy to the body of a living being. The heating and/or cooling device comprises a control unit and a heating and/or cooling pad which can be connected to the body of the living being and is provided with a heating and/or cooling element, which control unit and pad are electrically and mechanically connected to one another, a control signal being generated by means of the control unit, by means of which control signal the energy output from an energy source to the heating and/or cooling element can be controlled.

In addition, the posture sensors can be used to measure the posture of the person and determine said posture in the control unit, from which the open-loop and/or closed-loop control signal can be calculated in order to control the heat output so that the posture is corrected.

A computer program having a program code for carrying out the above method when the computer program runs on a computer or processor is also provided.

BRIEF DESCRIPTION OF THE DRAWINGS

Embodiments of the present invention are explained in more detail with reference to the enclosed drawings, in which:

FIG. 1 is a schematic illustration of a first embodiment of a heating and/or cooling device in a plan view;

FIG. 2 is a schematic illustration of a second embodiment of a heating and/or cooling device having three connecting elements in a plan view;

FIG. 3A is a further schematic illustration of a heating and/or cooling device in a side view with a connected heating and/or cooling pad and control unit;

FIG. 3B is a further schematic illustration of a heating and/or cooling device in a side view with a separated heating and/or cooling pad and control unit;

FIG. 4 is a further schematic illustration of a heating and/or cooling device in a lateral sectional view with a separated heating and/or cooling pad and control unit;

FIG. 5A shows a person in a front view with a plurality of heating and/or cooling devices;

FIG. 5B shows a person in a rear view with a plurality of heating and/or cooling devices;

DETAILED DESCRIPTION OF THE PREFERRED EMBODIMENTS

Description of the Drawings

Figure 6:
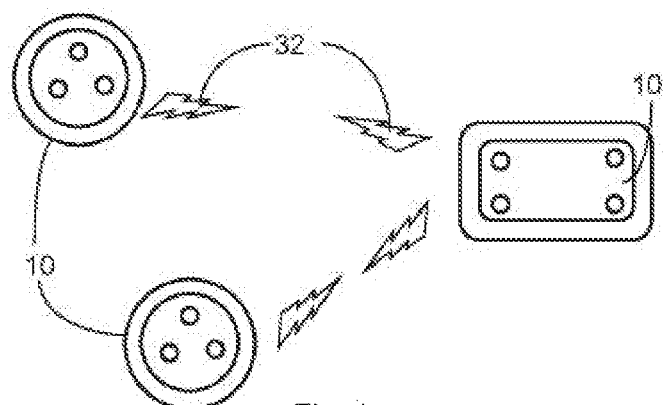
FIG. 6 shows a system for delivering heating and/or cooling energy to the body of a living being by means of various heating and/or cooling devices.

In the following description of the embodiments of the invention, identical or equivalent elements in the figures are provided with the same reference signs, so that their description in the different embodiments is interchangeable.

FIG. 1 is a schematic illustration in a plan view of a first embodiment of a heating and/or cooling device 10 for delivering heating and/or cooling energy to the body 28 of a living being. The heating and/or cooling device 10 comprises a heating and/or cooling pad 12 which can be connected to the body 28 of the person and has an upper face and a lower face, and on the lower face of which an adhesive surface 1210 is provided for attaching the heating and/or cooling pad 12 to the surface of the skin of the person. The adhesive surface 1210 can be formed on a first surface of the heating and/or cooling pad 12. The adhesive surface 1210 can be brought into contact with the surface of the skin of a living being. When the adhesive surface 1210 is brought into contact with the surface of the skin of the person, the adhesive surface of the heating and/or cooling pad should stick or adhere to the skin of the person. The adhesive surface 1210 can be protected with a protective layer of adhesive, e.g. against soiling or accidental attachment, before it is brought into contact with the surface of the skin. This protective layer is removed before attaching to the skin.

The adhesive used should have skin-friendly properties. This means that the adhesive surface 1210 or the adhesive should not damage or irritate the skin. Furthermore, it should be possible to easily remove the adhesive surface 1210 from the skin, for example after using the heating and/or cooling pad 12. The adhesive surface 1210 should be reusable.

The adhesive can preferably comprise a pressure-sensitive adhesive. Pressure-sensitive adhesives do not have a bonding mechanism. This means that they remain highly viscous and permanently tacky after being applied to a carrier material and are applied to a counterpart, e.g. the skin, by contact pressure and remain adhered there. The adhesive on the adhesive surface 1210 of the heating and/or cooling pad 12 can be gel-like. The adhesive on the adhesive surface of the heating and/or cooling pad 12 can be of high viscosity. The adhesive on the adhesive surface of the heating and/or cooling pad 12 can have a gel-like consistency. A gel-like adhesive can easily enter skin folds or unevenness on the skin and thus provide a good adhesive contact. The adhesive should have good thermal conductivity. Good thermal conductivity and good thermal contact between the heating and/or cooling pad 12 and the surface of the skin means that the heating and/or cooling energy can be easily transferred from the heating and/or cooling pad 12 to the body 28 or skin of the person.

The heating and/or cooling pad 12 can comprise at least one heating and/or cooling element 26 which converts electrical energy or electric current supplied by an electrical energy source 22 into heating and/or cooling energy or thermal energy. The heating and/or cooling element or the heating and/or cooling pad 12 can be designed to deliver or transmit the heating and/or cooling energy to the body 28 of the person. The heating and/or cooling element 26 can be heated by converting electrical energy into heating energy. The conversion of electrical energy or electric current into heating energy or thermal energy can be achieved, for example, by means of an electrical resistor (R) or an electrical heating element. The thermal energy generated is more or less proportional to the electrical energy used or output.

The heating and/or cooling energy can be delivered to the body 28 of the person, as is the case with a heat plaster. As a result of the delivery of heating and/or cooling energy, contracted muscles can relax particularly well. The delivery of heat can dilate the blood vessels in the muscles and can thus promote blood circulation in the muscle. Due to the improved blood circulation, harmful substances that block the muscle can also be flushed out of the muscle and the muscle can regenerate. By relaxing the muscles, cramps are released and pain is reduced.

The heating and/or cooling element 26 or the electrical resistor which converts the electric current into heat and/or cold can be arranged centrally on the heating and/or cooling pad 12 and distribute the heating and/or cooling energy on the heating and/or cooling pad 12 via a thermally well-conducting material such as metal. The heating and/or cooling element 26 can also be arranged flat on the heating and/or cooling pad 12 (shown in FIG. 1 by a dashed line). In this way, the electrical energy is converted into heating and/or cooling energy over a larger area on the heating and/or cooling pad 12. The heating and/or cooling pad 12 or the heating and/or cooling element 26 can comprise a heating film, wire, wire mesh or wire fabric. These can, for example, emit a constant heat and/or cold over more or less their entire surface.

Figure 10:
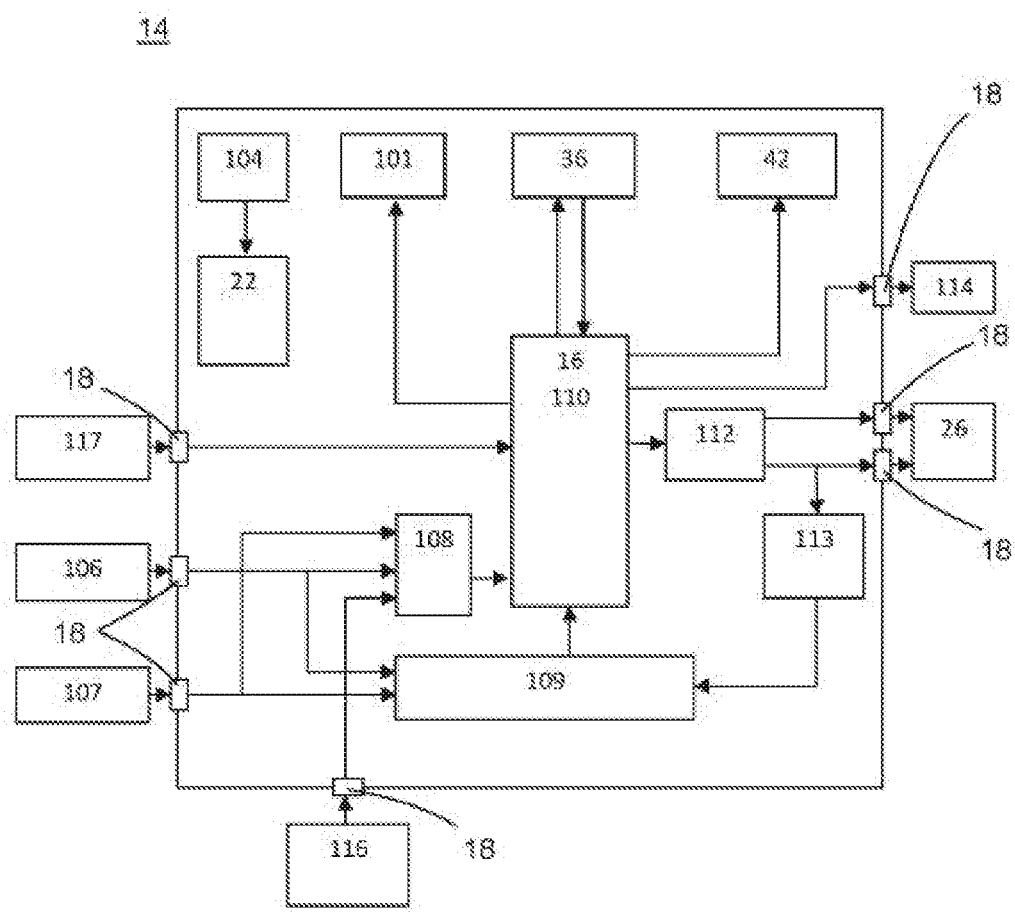
FIG. 10 is a schematic illustration of an embodiment of a control unit comprising a plurality of electrical components and one or more electrical connecting elements between the control unit and the heating and/or cooling support.

FIG. 10 is a schematic illustration of an embodiment of a control unit 14 comprising a plurality of electrical components and one or more electrical connecting elements 18a, 18b between the control unit 14 and the heating and/or cooling support 12 (not shown). The closed-loop/open-loop control unit 14 will be referred to as the control unit 14 in the following text. Said unit comprises:

- an energy source 22. The energy source 22 can be accommodated in the control unit 14 in either a fixed or a detachable manner. However, the energy source 22 can also be an externally arranged energy source 22, e.g. a power supply system, which is accommodated in the control unit 14 via a cable or contactlessly, for example by means of inductive or capacitive energy transfer. If a rechargeable battery is used as the energy source 22, the control unit 14 can also comprise a suitable charging circuit 104;
- a signal processing means as the signal processor 16, which means is configured to receive signals relevant to the operation of the control unit 14. Some of these signals 38, 107, 116, 117 may be electrical and come from outside the control unit 14, in which case the signal can be guided through an electrical connector 18. The signals 117 may be digital, in which case they can be processed directly by the signal processor 16. Some signal processors 16 may be able to process analog signals directly, but in most cases an analog-to-digital converter (ADC) 108 can be used to process external analog signals 38, 107, 116 to convert or adjust them accordingly;
- a control or microcontroller 110. This can be a separate component or combined with a signal processor 16 as shown in FIG. 10. The microcontroller 110 is configured and arranged to control the operation of the control unit 14; in particular the control unit 14 can be configured to control the energy output from the energy source 22 to one or more heating and/or cooling elements 26 via one or more electrical connectors 18. Some microcontrollers 110 may be able to provide the appropriate current and/or the appropriate voltage directly to the one or more heating and/or cooling elements 26, but in most cases a separate pulse width modulation (PWM) can be used—or example, PWM control by means of a pulse width modulator 112. In such a case, the microcontroller 110 can provide treatment instructions, such as heating the skin to 30° C. for 2 minutes; cooling to room temperature; repeating for 1 minute—the power control can then be configured to operate the one or more heating and/or cooling elements 26 using any suitable control algorithm, for example the transfer function of a PID controller;
- optionally, a display 101 can be provided for informing the operator about important parameters such as skin temperature, status of the battery 22 or operating mode;
- optionally, a vibration generator 42 can be contained in the control unit 14 as a means of providing stimulation other than heating and/or cooling. These additional means can be provided in the control unit 14, as shown, or outside the control unit 14 using an electrical connector 18 to provide electrical power to these additional stimulation means 114;
- optionally one or more skin temperature sensors 38 for preventing heat-induced and/or cold-induced damage to the skin. The signal processing means 16 and the control 110 can be configured to provide heat and/or cold during treatment stages only if the skin near the pad 12 is sufficiently not too hot and/or not too cold. For example, before supplying electrical power to one or more heating elements 26, an electrical current signal from the pulse width modulator 112 can be used to first check whether the skin is below a threshold temperature. After starting the heat treatment, the skin temperature can be continuously monitored and the treatment can be stopped if the skin temperature exceeds a preset threshold value. For example, before supplying one or more cooling elements 26 with an electrical current signal from the pulse width modulator 112, it can first be checked whether the skin is above a threshold temperature. Once the cooling treatment has started, the skin temperature can be continuously monitored and the treatment can be stopped if the skin temperature falls below a predetermined threshold value. Although they are shown outside the unit 14, other options can also be used inside the unit 14, such as a thermal imaging camera or an optical temperature detector mounted inside the unit 14 with an opening facing the skin. In general, a maximum temperature of approximately 42-43° C. is specified in order to avoid thermal damage to the skin. For this purpose, typical values during treatment are approximately 8° C. to 15° C., preferably also up to 20° C. These values can vary depending on the position on the body at which the treatment is applied and are individually dependent;
- optionally one of a plurality of skin detection sensors 107. The signal processing means 16 and the microcontroller-based control 110 can be configured to provide heat and/or cold during treatment steps only if the pad 12 is in sufficient contact with a skin surface. For example, before supplying electrical power to one or more heating and/or cooling elements 26, a measurement 107 can first be taken to ensure sufficient contact with the skin. Once treatment has started, the skin contact can be continuously monitored and the treatment can be stopped if the degree of skin contact falls below a predetermined threshold. Although shown outside unit 14, other options within unit 14 can also be used, such as a capacitive detector within unit 14. One or more skin temperature sensors 38 can also be configured as a skin detection sensor;
- optionally, but preferably, safety monitoring and a protection device 109. Under predetermined conditions during operation, the signal processing means 16 and the control 110 can be configured to change or even suspend the electrical energy supplied to the one or more heating and/or cooling elements 26, for example, as mentioned above, if a skin temperature is outside a predetermined range or if the degree of skin contact is below a predetermined threshold. Optionally, a current, voltage, energy and/or power monitor 113 can be provided to determine a dose on the skin; if the dose exceeds a predetermined value, the power of the electrical current signal of the pulse width modulator 112 can be changed or even suspended. Optionally, the unit 14 can comprise a memory that stores preset limits and ranges and it may be advantageous to allow the user to change or adjust these limits and ranges. Optionally, internal parameters can also be monitored, such as the temperature of the energy source 22 or the charge state of the energy source 22; for example, the signal processing means 16 and the control 110 can be configured to suspend or prevent treatment if there is insufficient energy in energy source 22 to complete the treatment; and optionally additional sensors 116, 117 such as one or more posture sensors, one or more EMG (electromyography) sensors, one or more bending sensors, one or more 3D gyro sensors, one or more acceleration sensors, or one or more strain gauges.

The signal processor 16 may be designed to generate a control signal to the control 110 of an electrical power source. The signal processor 16 can be designed to receive and process signals from one or more signal sources 38, 107, 116, 117 e.g. posture sensors, temperature sensors 38 or other sensors. The signal processor 16 can generate a control signal by means of which the electrical energy source is controlled or the energy supply or energy delivery to the body or muscles is controlled. The signal processor 16 can comprise a processing means or a computing unit. The signal processor 16 can also process the signals partially or not at all and forward the signals for processing to another signal processor, e.g. in a mobile device, or to another heating and/or cooling device 10 or control unit 14. The signal processor 16 can, for example, only receive and/or transmit radio signals.

The heating and/or cooling element 26 may be designed to receive electric current directly from the electrical energy source 22 and to deliver the heating and/or cooling energy to the skin of a living being. The heating and/or cooling element 26 may also be designed to receive the electric current from the electrical energy source 22 via the signal processor 16 and microcontroller 110 and to deliver the heating and/or cooling energy to the skin of the person. In addition, the signal processor 16 can transmit the control signal for controlling 110 the electrical energy source 22 to the heating and/or cooling pad 12 and the heating and/or cooling pad 12 can transmit the signal to the electrical energy source 22 and receive the electrical energy from the electrical energy source 22.

The electrical energy source 22 and the heating and/or cooling element 26 may be designed to heat the heating and/or cooling pad 12 by 20 K in less than 1 minute, preferably in less than 20 seconds, particularly preferably in less than 5 seconds. The heating of the heating and/or cooling pad 12 can be monitored by a temperature sensor 38 in order to avoid skin injuries such as burns. The temperature sensor 38 can be placed on the heating and/or cooling pad 12 and can monitor the temperature of the heating and/or cooling pad 12, for example. The signal processor 16 can, for example, process a measured value from the temperature sensor 38 and, depending on the measured value or temperature value measured at the temperature sensor 38, change the control signal for controlling the electrical energy source 22 so that more electrical energy is fed to the heating and/or cooling pad 12 if the heating and/or cooling pad 12 should be heated more and less or no electrical energy is fed to the heating and/or cooling pad 12 if the heating and/or cooling pad 12 should be heated less or not at all. The temperature sensor 38 can also measure the skin temperature or body temperature of the person and, depending on the body temperature, control the electrical energy as described above so that the heating and/or cooling device 10 warms the person as soon as the skin temperature or body temperature falls below a predetermined value.

The time until the skin is heated and/or cooled depends on a number of parameters, including:

the time taken for the heating and/or cooling pads 12 to reach the desired temperature and the rate of heat transfer between the pads 12 and the adjacent skin;

the current, voltage and energy output of the pulse width modulation power control 112;

the maximum current, the maximum voltage and the maximum energy output of the energy source 22;

the type of heating and/or cooling elements 26;

the dimensions of the heating and/or cooling elements 26;

for a heating element 26, the resistance and the dimensions of the heating conductors (suitable metals include copper, aluminum, platinum or chromium of alloys of these metals);

for a heating element 26, the density (distance) of the heating conductors. In embodiments in which one or more resistance heating elements are connected from the center of the pad 12, the central part of the pad will likely heat faster than the edges of the pad;

the service control profile—e.g. PID control is usually based on the error between the actual values and the target value. However, the initial heating and/or cooling can be accelerated by exceeding the threshold of the PID controller at the beginning. For example, the desired value can be increased by 1 or 2° C.; if the target value is actually 42° C., a heating element can be given an overshoot value of 44° C. or even 45° C. Although for safety reasons the skin temperature is usually maximized at 42° C. or 43° C., a higher temperature can be tolerated for a very short period of time, such as 45° C. for no more than 5 seconds. By appropriate optimization, temperatures of up to 42° C. near the middle of pad 12 were achieved within 20 seconds.

The electrical energy source 22 can be, for example, a mobile electrical energy source such as a battery or accumulator. The battery or accumulator can emit electrical energy or electric current. An accumulator can be charged or recharged with electrical energy via a further energy source 22 and a charging circuit 104. The electrical energy source 22 can also be a public power supply system, in which case, for example, the voltage of the power supply system can be reduced via a power supply unit before being fed into the heating and/or cooling device 10.

The heating and/or cooling pad 12 and the control unit 14 can be electrically and mechanically connected to one another by at least one electrical connector 18, via which the electrical energy can be transmitted to the heating and/or cooling element 26, and at least one magnetic connector 20.

An electrical connecting element 18a can be arranged on the control unit 14 for transmitting the electrical energy or an electric current from the control unit 14 to a complementary electrical connecting element 18b which is formed on the heating and/or cooling pad 12. The electrical connector 18 can be connected to the electrical energy source, the signal processor 16 or, for example, a control element which receives the control signal for controlling 110 the electrical energy source 22. The electrical connector 18 can be designed, for example, as an electrical plug and electrical socket or in the form of magnets. The electrical connecting elements 18a, 18b are preferably made of metal. The electrical connecting elements 18a, 18b can also be coated with another metal which has a low contact resistance or does not oxidize (e.g. gold). The electrical connectors 18 can be arranged mechanically fixedly on the control unit 14 and/or on the heating and/or cooling pad 12 for the transmission of electrical energy. The electrical connectors 18 can also be connected to the control unit 14 and/or the heating and/or cooling pad 12 via a flexible cable.

At least one mechanical connecting element 20a may be arranged on the control unit 14. In addition to the mechanical connecting element 20a arranged on the control unit 14, a complementary mechanical connecting element 20b can be arranged on the heating and/or cooling pad 12. The mechanical connecting element 20b can be arranged on the heating and/or cooling pad 12 on the upper face opposite the adhesive surface on the heating and/or cooling pad 12. The mechanical fastening element 20a on the control unit 14 should be aligned with the position of the mechanical fastening element 20b on the heating and/or cooling pad 12 so that the fastening elements 20a, 20b can be easily connected.

By means of the mechanical connectors 20a, 20b, the control unit 14 and the heating and/or cooling pad 12 can be easily combined to form a heating and/or cooling device 10. Conversely, the heating and/or cooling device 10 can be divided or separated by the magnetic connectors 20 into a control unit 14 for use in a heating and/or cooling device 10 according to the embodiment and into a heating and/or cooling pad 12 for use in a heating and/or cooling device 10 according to the embodiment. In FIG. 1, the control unit 14 and the heating and/or cooling pad 12 are connected by two magnetic connectors 20.

The heating and/or cooling pad 12 can be a disposable element which can be replaced after being used once or more, approximately ten times or approximately twenty or thirty times. On the one hand, this has advantages with regard to hygiene, as the heating and/or cooling pad 12 is stuck directly onto the body or skin of the person and sometimes comes into contact with a lot of body sweat and fat. On the other hand, when the adhesive effect diminishes, the adhesive surface of the heating and/or cooling pad 12 can be replaced by replacing the heating and/or cooling pad 12 to achieve a good adhesive effect of the heating and/or cooling device 10 on the body 28 of the person again. It is also possible, for example, for the heating and/or cooling element 26, which converts electrical energy into thermal energy, to be removed from a used heating and/or cooling pad 12 and inserted into another, new heating and/or cooling pad 12. Costs and resources can be saved by reusing the heating element 26 or sensors on the heating and/or cooling pad 12.

The control unit 14 can be a reusable element. The control unit 14 can comprise, for example, the signal processor 16, a radio unit, the electrical energy source 22 or other electronics. The control unit 14 should comprise components that can be easily recycled and/or are expensive or valuable. All the intelligence or components contributing to the intelligence of the heating and/or cooling device 10 can be arranged on the control unit 14. The control unit 14 can be reused as often as required, thus saving costs and resources.

The control unit 14 can be positioned on the heating and/or cooling pad 12 in such a way that it does not come into direct contact with the skin of the person when the heating and/or cooling device 10 is worn or when it is attached to the body 28 of a living being. This results in less unhygienic contamination of the control unit 10, e.g. by sweat or body fat.

The electrical connector 18 has a first electrical connecting element 18a connected to the control unit 14 and a second connecting element 18b connected to the heating and/or cooling pad 12. The magnetic connector 20 further comprises a first mechanical connector 20a connected to the control unit 14 and a second mechanical connector 20b connected to the heating and/or cooling pad 12. The first and second mechanical connecting element 20a; 20b can comprise the corresponding first and second electrical connecting element 18a; 18b, respectively. The mechanical connecting element 20a, 20b can comprise the electrical connecting element 18a, 18b for the transmission of the electric current. In other words, the electrical connecting element 18a, 18b for the transmission of the electric current can be integrated e.g. in the mechanical connecting element 20a, 20b. The mechanical connecting element 20a, 20b can also be integrated e.g. in the electrical connecting element 18a, 18b for transmitting the electric current. A metal push button having a corresponding counterpart or a metal magnet, for example, can be used both as a mechanical connecting element 20a, 20b and as an electrical connecting element 18a, 18b for transmitting the electric current.

Embodiments of a heating and/or cooling device 10 can, as a smart heat plaster, be self-adhesive and, as a heating and/or cooling element in the heating and/or cooling pad 12, comprise a heating film or wire mesh, which can be heated by energy to the therapeutic heat of 40° C. to 42° C. within seconds.

The self-adhesive film of the heating and/or cooling pad 12 can be used several times, preferably twenty to thirty times. Moreover, it has proven to be particularly advantageous in the context of the invention if, in the embodiments of the invention, a particularly skin-friendly adhesive is used for the self-adhesive film, such that the heating and/or cooling pad 12 can be applied in a manner similar to that of a temporary tattoo and can also remain on the skin overnight or for several days. This is particularly advantageous, as the other components of the heating and/or cooling pad 10 can be placed on the heating and/or cooling pad 12 only when treatment is required and can be removed again after treatment.

FIG. 2 shows a heating and/or cooling device 10 having three mechanical connecting elements 20a, 20b. The heating and/or cooling device 10 can comprise at least three mechanical connecting elements 20a, 20b, three mechanical connecting elements 20a being formed on the control unit 14 and three complementary mechanical connecting elements 20b being formed on the heating and/or cooling pad 12 at the same location on the opposite side for connecting the heating and/or cooling pad 12 to the control unit 14. The mechanical connecting elements 20a, 20b can also comprise the electrical connecting elements 18a, 18b. The mechanical connecting elements 20a, 20b can thus be arranged in a mirror-inverted manner between the control unit 14 and the heating and/or cooling pad 12.

By positioning the mechanical and/or magnetic connecting elements 20a, 20b, for example, alignment coding can be achieved so that the control unit 14 can be connected to the heating and/or cooling pad 12 only in a certain position or location (coding). This makes it easier, for example, to absorb certain forces, e.g. vertical forces, which act on the heating and/or cooling device 10 when worn on the body 28 of a living being. Furthermore, by means of coding for the connecting elements 18a, 18b; 20a, 20b, which comprise both mechanical connecting elements 20a, 20b and electrical connecting elements 18a, 18b, the risk of electrical polarity reversal when connecting the heating and/or cooling pad 12 to the control unit 14 can be reduced. Furthermore, with three pairs of connecting elements 18a, 18b; 20a, 20b, in addition to the two-pole electrical supply, a control signal can be transmitted on the third connecting element. In the case of a control signal modulated on the two-pole electrical supply signal, the need for a third pair of connecting elements 18a, 18b; 20a, 20b. However, more than three, e.g. four or more, mechanical connecting elements 20a, 20b and/or electrical connecting elements 18a, 20b can connect the heating and/or cooling pad 12 and the control unit 14 to form a heating and/or cooling device 10.

FIGS. 3a and 3b are each another illustration of an embodiment of the heating and/or cooling device 10 in a side view. FIG. 3a shows the heating and/or cooling device 10 having a connected or coupled heating and/or cooling pad 12 and control unit 14. In the coupled state, no distinction can be made in the illustration between electrical or mechanical and/or magnetic connecting elements 18a, 18b; 20a, 20b which are attached to the control unit 14 or to the heating and/or cooling pad 12. The heating and/or cooling pad 12, which can be connected to the body of the person, has an upper face 122 and a lower face 121, on which lower face the adhesive surface 1210 is provided for attaching the heating and/or cooling pad 12 to the surface of the skin of the body 28. The heating and/or cooling pad 12 comprises at least the heating and/or cooling element 26, which can convert electrical energy output from the electrical energy source 22 into heating and/or cooling energy. The control unit 14 can comprise the signal processor 16 for controlling the energy output from the energy source 22 to the heating and/or cooling element 26.

FIG. 3b shows the heating and/or cooling device 10 having a separated heating and/or cooling pad 12 and control unit 14. Two electrical connecting elements 18a and two mechanical connecting elements 20a are shown on the control unit 14. The mechanical and/or magnetic connecting element 20a encloses or encompasses the electrical connecting element 18a for transmitting the electric current. The connecting elements can thus be mechanical and/or magnetic 20a and/or electrical 18a connecting elements. Electrical connecting elements 18b and mechanical and/or magnetic connecting elements 20b that are complementary to the connecting elements 18a, 20a of the control unit 14 can be arranged on the heating and/or cooling pad 12. The mechanical and/or magnetic connecting element 20b encloses or encompasses the electrical connecting element 18b for transmitting the electric current in the illustration.

The adhesive surface 1210 can be formed on a lower face 121 or first surface 121 of the heating and/or cooling pad 12. The electrical or mechanical and/or magnetic connecting elements 18b, 20b can be arranged on an opposite upper face 122 or second surface. The heating and/or cooling pad 12 in turn comprises at least the heating and/or cooling element 26. The heating and/or cooling element 26 can convert electrical energy output by the electrical energy source 22 into heating and/or cooling energy. The control unit 14 can comprise the signal processor 16 for controlling the energy output from the energy source 22 to the heating and/or cooling element 26.

FIG. 4 is another schematic illustration of a heating and/or cooling device 10 in a lateral sectional view having a separated heating and/or cooling pad 12 and control unit 14. The sectional view shows various elements which may include the control unit 14 and the heating and/or cooling pad 12.

The electrical energy source 22 can be arranged or attached in or on the control unit 14, for example. It is also possible to arrange or attach the electrical power source 22. This means that the electrical energy source 22 can be rigidly connected to the control unit 14 or removable. The electrical energy source 22 can be designed to supply electrical energy to the heating and/or cooling pad 12 and/or the control unit 14. This means that the heating and/or cooling device 10 is independent of a wired electrical power supply, which would have to be connected to a socket, for example, and restricts the freedom of movement of the person. The mobile electrical energy source 22 can be e.g. a battery or an accumulator. The battery or accumulator can output electrical energy or electric current. An accumulator can be charged or recharged with electrical energy via a further energy source 22 and a charging circuit 104. The heating and/or cooling device 10 can also be connected to a socket, for example via a power supply unit, for energy supply in embodiments. The heating and/or cooling device 10 can thus be connected to an externally arranged energy source. By supplying the heating and/or cooling device 10 with electrical energy from a socket, the electrical energy source does not need to be replaced or recharged.

The heating and/or cooling device 10, preferably the control unit 14, can comprise a posture sensor 24, it being possible to design the posture sensor 24 to at least partially detect the posture and/or movement of the person and to generate posture data. The signal processor 16 can be designed to control the energy output from the energy source 22 to the heating and/or cooling element 26 by means of the posture data. The heating and/or cooling pad 10 can comprise only one posture sensor 24 or a plurality of posture sensors 24. A plurality posture sensors 24 can usually detect the posture more precisely. The posture sensor 24 or the signal processor 16 can detect whether the person has poor or incorrect posture or whether the posture is correct or rather correct. The posture data can be generated based on the posture. The posture data can be an analog or digital electrical signal generated by the posture sensor 24. The signal can be provided or output from the posture sensor 24 as a wired signal on an electrical line or a wireless signal or radio signal.

The posture sensor 24 can be arranged on or in the control unit 14. The posture sensor 24 can also identify or detect the posture using skin data. The posture sensor 24 can comprise a 3D gyro sensor (Gyroscope 3D), acceleration sensor, temperature sensor 38, bending sensor, EMG sensor, strain gauges or other sensors for detecting posture. The posture sensor 24 can be used to detect the posture of the person. Posture sensors 24 can, for example, be placed on the shoulders or neck or in the region of the spine and detect the posture of the person. A 3D gyro sensor or a 3D gyroscope such as the ITG-3200 from IvenSens Inc. can detect movements in three axes and thus determine the position in space. A change in position in space can be detected by an acceleration sensor or an accelerometer sensor such as the BMA400 from Bosch. There are also sensors that combine the two functions described above, e.g. the MO 416.H1X or the MO416.H13 from Makersan.

A bending sensor 241 can also preferably be arranged as posture sensor 24 on the heating and/or cooling pad 12, which is positioned closer to the body than the control unit 14. Bending sensors 241 can detect the posture in particular in the region of the shoulders and the spine and can easily detect a curvature of the spine or a lifting or falling of the shoulders. The bending sensor 241 can have a length of 5 cm to 40 cm. Bending sensors 241 preferably have a length of 10 cm to 30 cm. Long bend sensors 241 can be arranged in the region of the spine, for example, and can detect said spine over the entire length thereof from the coccyx to the cervical vertebrae. Furthermore, bending sensors 241 can detect the posture at the shoulders, for example from the left arm to the right arm. A bending sensor 241 can also be placed on the left shoulder and on the right shoulder. Instead of single long bending sensors 241, several shorter bending sensors 241 with a length of e.g. 1 cm to 5 cm, preferably 2 cm to 3 cm, can be arranged at the described points, for example. A bending sensor 241 such as the SEN-10264 from Spectra Symbo can be used to detect curvatures of the spine, for example, or a rising or falling shoulder. The bending sensor is a narrow strip of 7.3 cm in length and 6.3 mm in width. At rest the applied resistance is 25 kOhm. The more the sensor is bent, the more the resistance increases, which can be a maximum of 125 kOhm.

This means that posture sensors 24 can be used to detect e.g. deformations in posture. Deformations in terms of posture are, for example, a hump, a hollow back, shoulder tension, or misalignment of the shoulders or back. The posture of the person can then be determined from the measured values of the various posture sensors.

In addition, the control unit 14 can comprise the signal processor 16. The signal processor 16 can be arranged on or in the control unit 14. The signal processor 16 can be, for example, a processing means or a processing unit. The processing means can also be integrated, for example, in a device specializing in improving posture, in particular on a mobile device. The processing means can also be integrated in a universal mobile device such as a tablet or a smartphone or another mobile device. It is often no longer possible to distinguish between specialized or universal mobile devices, since functions can often be provided via the software in the mobile device. Specialized or universal mobile devices usually comprise at least one input unit, a display, a processing means, sensors, communication means and an energy storage device.

Depending on the posture data or the signal from the posture sensor 24, the signal processor 16 can determine the posture. Depending on the posture determined by the signal processor 16, the signal processor 16 can generate a control signal for controlling an electrical energy source 22. The control signal for controlling the electrical energy source 22 can in turn be an analog or digital electrical signal, which is generated by signal processor 16. The signal can be provided or output by the signal processor 16 as a wired signal on an electrical line or as a wireless signal or radio signal. The signal processor 16 can also directly output more or less electrical energy which has been generated or stored by an electrical energy source 22.

The signal processor 16 can be designed to receive the posture data. The signal processor 16 can be designed to receive the posture data as a signal or electrical signal. The signal can be a wired signal on an electrical line or a wireless or radio signal. Preferably, the reception of the signal at the signal processor 16 is coordinated with the output of the signal of the posture sensor(s) 24, 241.

The heating and/or cooling pad 10 or the control unit 14 can comprise a radio unit 36 for transmitting and/or receiving data. The radio unit can be arranged on the control unit 14. The radio unit 36 can also be integrated or arranged in the signal processor 16 or a processing means, for example. The radio unit 36 can exchange data between heating and/or cooling devices 10 and/or a mobile device. All the electronics (except some sensors) can be located on the control unit 14.

The heating and/or cooling pad 12 can be designed to receive electric current from the electrical energy source 22 or from the signal processor 16. The heating and/or cooling pad 12 can be connected to the electrical energy source 22 or the signal processor 16 via electrical lines which can transmit the electrical energy or current. The heating and/or cooling pad 12 can include temperature sensors 38, bending sensors 241, electrodes 40, heating and/or cooling element 26 (heating film/heating wire mesh), an adhesive surface 1210 with adhesive and connecting elements 18b, 20b.

The heating and/or cooling pad 12 can at least partially convert the electrical energy into thermal energy and deliver it to the body 28 of the person. The delivered thermal energy can have a relaxing or stimulating effect on the muscles and can improve the posture of the person.

The energy which is delivered to the body by one or more heating and/or cooling pads 12 can also influence other body tissues such as fatty tissue. In particular the contraction of muscles can activate the burning of fatty tissue in the body. This can also increase the well-being of the person and improve posture.

For example, the heating and/or cooling element 26 or the heating element in the heating and/or cooling pad 12 may comprise a film, the film being capable of converting electrical energy into thermal energy over more or less its entire surface. As a heating film, for example, electrically heatable polyamide film such as the RS film from Kapton can be used. The heating film enables a constant and effective heat exchange. The heating and/or cooling element 26 can also include e.g. electrical conductors or a wire mesh and is designed to deliver constant heat with lower energy consumption. The heating and/or cooling element 26 can also convert electrical energy into thermal energy in a relatively small space and distribute the heat over a larger area in or on the heating and/or cooling pad 12 via a good thermal conductor, such as a metal plate.

Electrodes 40 can be arranged on the heating and/or cooling pad 12 and the signal processor 16 can be designed to determine the muscle tension by electromyography. The electrodes 40 can be used to measure potential changes of a muscle or muscle group. The signal processor 16 can generate a control signal for controlling the electrical energy storage device 22, which signal is dependent on the muscle tension. If the muscle is tense, for example, the heating and/or cooling device 10 can be warmed up by delivering electrical energy from the electrical energy storage device 22 to the heating and/or cooling pad 12. The heating can stimulate muscles.

The skin resistance can also be determined using the electrodes 40. By measuring the voltage between the two electrodes, the conductance, the resistance or the impedance between the electrodes 40 and the skin of the person can be determined by a current flowing from a first electrode 40 to a second electrode 40, for example. The conductance or the resistance value can also be used for controlling 110 the heating and/or cooling energy by means of the signal processor 16 at the heating and/or cooling device 10.

The heating and/or cooling device 10 can comprise a vibration generator 42, which is designed to convert electrical energy emitted by the electrical energy source 22 into mechanical energy and to deliver mechanical energy to the body of the person. Mechanical energy can be transmitted to the skin or body of the person in the form of vibrations. The vibrations can be generated by a vibration generator 42 which comprises, for example, an electric motor and an imbalance. In the case of an imbalance, the center of gravity is not on the axis of rotation. The vibration generator can also be a linear motor that moves a mass back and forth, thereby generating vibrations. The vibrations can give the person an indication of, for example, posture, or relax or loosen muscles by massage.

The heating and/or cooling device 10 or the heating and/or cooling pad 12 can also comprise a temperature sensor 38. Depending on the arrangement on the heating and/or cooling device 10 or the heating and/or cooling pad 12, the temperature sensor 38 can detect the skin temperature or body temperature of the person. The temperature sensor 38 can also detect the temperature of the heating and/or cooling pad 12. The temperature sensor 38 can be connected to the signal processor 16 and provide temperature data to the signal processor 16 based on the measured temperature value of the temperature sensor 38. Depending on the temperature data, the signal processor 16 can generate the control signal for controlling 110 the electrical power source 22. Depending on the temperature value detected by the temperature sensor 38, the energy output from the energy source 22 to the heating and/or cooling element 26 can thus be controlled or the electrical energy supply for the heating pad 12 can be controlled.

Both the heating and/or cooling pad 12 and the control unit 14 are depicted as round in FIG. 1. If standard gel pads having a diameter of 80 mm are used, the control unit 14 is preferably designed for a smaller diameter—approximately 60-70 mm, preferably 62-68 mm.

However, the heating and/or cooling pad 12 and the control unit 14 can also have an oval or polygonal shape. Both the heating and/or cooling pad 12 and the control unit 14 can also have a rectangular or square shape, for example with pointed or rounded corners. Both the heating and/or cooling pad 12 and the control unit 14 can have any shape. The heating and/or cooling pad 12 and the control unit 14 can also have different shapes. For example, the control unit 14 can be round and the heating and/or cooling pad 12 has an elongate rectangular shape.

Figure 9:
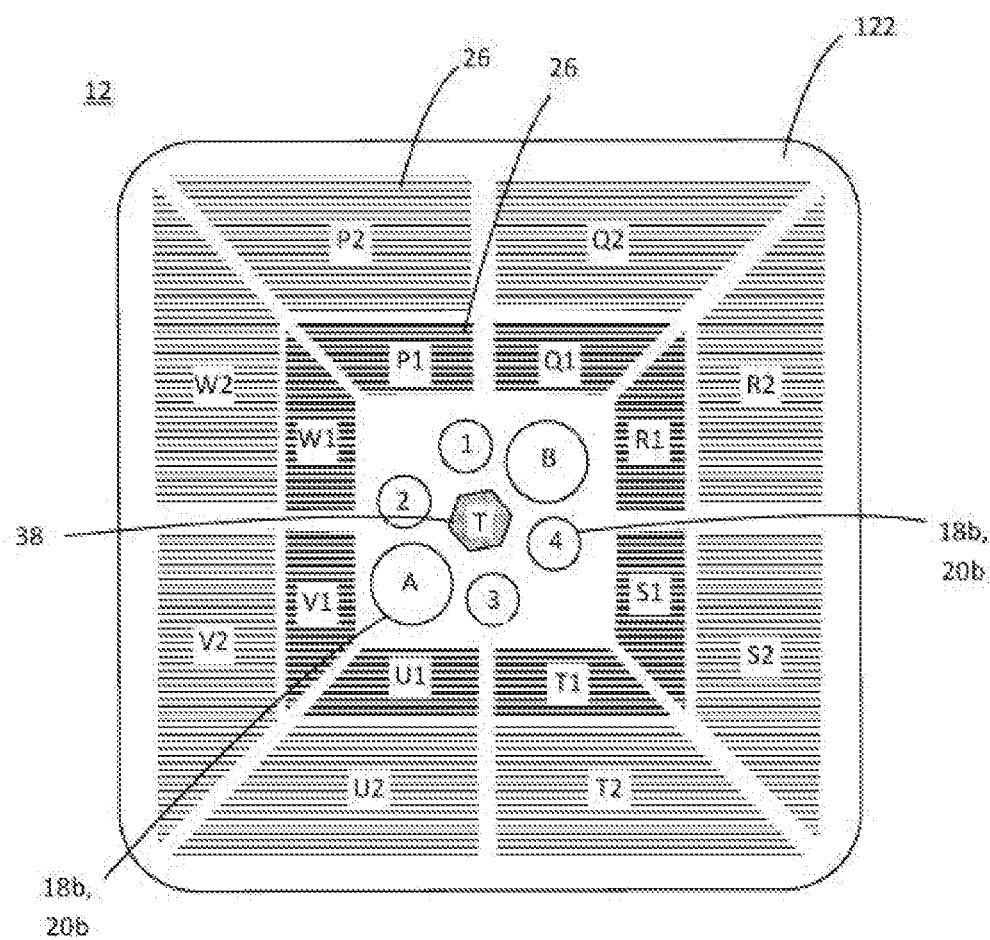
FIG. 9 shows a heating pad, which comprises heating elements having resistive conductors.

FIG. 9 shows a heating pad 12, which comprises heating elements 26 having resistive conductors. The drawing is a view from above of the upper face 122 of the heating pad. For reasons of clarity, not all features are shown.

The overall shape of the heating pad 12 is approximately square with rounded corners. In this configuration, eight approximately triangular heating elements 26 are provided: P, Q, R, S, T, U, V and W. Each extends from a position near the center to a position closer to the periphery of the pad 12. Each of the eight heating elements 26 is further divided into two parts: a portion near the center of the plate 12, with the conductors being relatively close together (a small distance)—these are the regions P1, Q1, R1, S1, T1, T1, U1, V1 and W1—and another portion near the periphery of the pad 12, with the conductors being relatively far apart (a larger distance)—these are the regions P2, Q2, R2, S2, T2, U2, V2 and W2. The portions of each heating element 26 are electrically connected: P1 and P2/Q1 and Q2/R1 and R2/S1 and S2/T1 and T2/U1 and U2/V1 and V2/W1 and W2. This means that when a current is applied to each of the heating elements 26, the portions near the center heat up more quickly than the peripheral portions.

In the middle of the pad 12 there are six electrical 18*b* and magnetic connections 20*b* having two different sizes: two larger connections A & B, and four smaller connections 1, 2, 3, 4. In this configuration, the 18*b*, 20*b* connections have an axis of symmetry, such that the pad 12 can be connected in one of two directions. The use of two much larger A, B connections (about twice the diameter of the smaller connections 1, 2, 3, 4) means that other orientations and possible incorrect connections are at least less likely and some incorrect connections become impossible.

A temperature sensor marked T is also in the center, which sensor is configured and arranged for measuring the temperature 38 near the skin.

For reasons of clarity, the control unit 14 is not shown, but has corresponding electrical 18*a* and magnetic 20*a* connecting elements which correspond to the connecting elements 18*b*, 20*b* shown. These connections therefore create a physical and electrical connection by coating appropriately dimensioned magnets with a conductive metal such as chrome, gold or platinum. A suitable cover plate (not shown) can be provided on the upper layer 122 of the heating pad 12—with openings having the same dimensions as the control units 14 connections 18*a*, 20*a* or the heating pad 12 connections 18*b*, 20*b*, recesses are provided for making it easier to align the two parts of the connections 18*a* to 18*b* and 20*a* to 20*b*.

Depending on the number of different electrical connections required, one or more of the magnetic connecting elements 20*a*, 20*b* can be configured as a purely magnetic connection and not also as an electrical connection—e.g. connections A and B can be exclusively magnetic 20*a*, 20*b*, while 1, 2, 3, 4 are both magnetic 20*a*, 20*b* and electrical 18*a*, 18*b*, 18*b*, which create four different electrical connections between the control unit 14 and the heating pad 12.

In the simplest configuration, all heating elements 26 are operated in parallel and require only two electrical connecting elements 18*a*, 18*b*. To avoid undesired heating of the connecting elements 18*a*, 18*b*, more than one connection can be used for each channel—for example A, 1, 2 connected to one side of each heating element 26 and B, 3, 4 connected to the other side of each heating element 26.

In the embodiment shown, six different electrical connecting elements are provided. By connecting each electrical connecting element 18*b* to at least two heating element terminals, it is possible to set and adjust the electrical energy in each heating element 26:

1 to A=>heating element P (26)
1 to B=>heating element Q (26)
2 on A=>heating element R (26)
2 on B=>heating element S (26)
3 to A=>heating element T (26)
3 to B=>heating element U (26)
4 on A=>heating element V (26)
5 on B=>heating element W (26)

As the heating pads 12 have to be disposed of after a number of applications, it may be helpful to keep the number of connecting elements and consequently of connectors as low as possible to reduce costs.

In the configuration of FIG. 9, the heating elements 26 were located in different, consecutive segments that extend around the periphery of the heating pad 12. Alternatively or additionally, different concentric heating elements 26 can be provided.

The temperature sensor 38 (T) can use two or more of the electrical connections 18*b*, depending on the sensor type and the number of control signals to be supplied by the parking heater 26.

A similar configuration can also be provided for a cooling pad if the resistance conductors have been replaced by appropriately dimensioned cooling elements 26 such as Peltier elements.

FIGS. 5*a* and 5*b* show a person with several heating and/or cooling devices 10 stuck or attached to the body 28. FIG. 5*a* shows the person in a front view. One heating and/or cooling device 10 is placed on each of the right and left thighs. Two other heating and/or cooling devices 10 are placed above the chest. The heating and/or cooling devices 10 can be placed or stuck anywhere on the body. Preferably, the heating and/or cooling devices 10 can be placed on the skin over underlying muscles or muscle groups which are cramped or tensed. The heat of the heating and/or cooling devices 10 can help to relax the muscles. The heating and/or cooling device 10 can also be used at all trigger points of the body (e.g. thighs, back, etc.)

In medicine, the following effects are attributed to heat: muscle relaxation, improvement of blood circulation, reduction of the viscosity of the synovial fluid, improvement of the elasticity of the collagenous connective tissue, and pain relief. The heating and/or cooling devices 10 can combat or relieve pain or tension where it occurs. Heat therapies should not be used in inflammatory processes, for example in inflammatory rheumatism (acute flare-up) and in acute diseases that are accompanied by the body's own heat generation (local inflammation, redness, overheating, fever).

The heating and/or cooling device 10 should be positioned on the body 28 of the person in such a way that contracted muscles located under the skin of the body 28 are stimulated, i.e. can be supplied with heating and/or cooling energy from the heating and/or cooling device 10. By means of the heating and/or cooling device 10, energy or heating and/or cooling energy can be delivered to the person's body 28 or to contracted muscles. The more precisely the heating and/or cooling device 10 is placed over contracted or tense muscles, the more precisely the energy can be delivered to the contracted muscle. Wastage due to unnecessary energy release can thus be reduced in places where there are no tense muscles and the total energy consumption can be reduced by efficient use of energy. The batteries therefore last longer. Preferably, the heating pad 10 is placed as close as possible to or directly on the body in order to transfer the energy to the body with as little loss as possible.

The heating and/or cooling device 10 can be placed in the region of the neck or spine. In the region of the neck and/or the spine, tensions or cramps or persistent contractions of the musculature often occur. The heating and/or cooling devices 10 supply thermal energy to the affected areas or muscles, which relaxes them. The muscle in the body of the person can thus decontract. The energy supplied to the body of the person can cause a change in the contraction of the muscles under the person's skin. By placing it in this region, the energy can be delivered to the affected regions with tension with little wastage.

The heating and/or cooling devices 10 can also be placed on parts of the body to allow conclusions to be drawn regarding the posture of the person, e.g. on the shoulders or spine or near the shoulder or spine. Of course, at least one posture sensor can also be located in each of the shoulder region and the back region. The neck, shoulder and spine region is particularly suitable for detecting the posture of the person. Preferably, the posture sensors are positioned as close as possible to or directly on the body in order to keep measurement errors in the acquisition of posture data as small as possible or to avoid measurement errors.

The heating and/or cooling devices 10 can also be used for different heat therapy scenarios (trigger point treatment). Here, heat is delivered at trigger points on the body. The signal processor(s) can generate control signals according to a predefined pattern for controlling the energy output from the energy source to the heating and/or cooling element in different heating and/or cooling devices 10. During treatment, the heating and/or cooling device 10 can be heated for a short time. Due to the arrangement of the heating and/or cooling devices 10 and successively warming up the heating and/or cooling devices 10, a kind of thermal wave movement can be generated on the body 28 of the person, for example. This means, for example, that a plurality of heating and/or cooling devices 10 more or less in a line are switched on one after the other. By successively switching on or warming up the heating and/or cooling devices 10, a kind of wave movement is generated on the body 28 of the person or the coordinated warming-up of the heating and/or cooling devices 10 creates the impression of a heat wave that continues or spreads from one point. This wave-like heat delivery to the body can be used to achieve a particularly effective relaxation of the muscles. A first heating and/or cooling device 10 can, for example, be supplied with electrical energy for between 5 minutes and 2 hours, preferably between 20 minutes and 1 hour, and thus kept warm. A second heating and/or cooling device 10 is then supplied with electrical energy for a similar period of time and thus kept warm. The first or a third or further heating and/or cooling device 10 can then be heated and kept warm again.

A heating and/or cooling pad 14 can be continuously supplied with a specified energy, e.g. a specified voltage (e.g. 5 volts (V)) or a specified current. The heating and/or cooling pad 14 can be supplied with a lower voltage (e.g. 3 V) or higher voltage (e.g. 7 V) or current for controlling 110 the heat. It is also possible to control the heating and/or cooling pad 14 with a constant current or voltage and by changing the on/off time (pulse-pause ratio) in the heating of said pad. For example, the heating and/or cooling pad 12 can be supplied with electrical energy for 2 seconds and not supplied with electrical energy for 1 second. The heating of the heating and/or cooling pad can be controlled by the ratio of the time between energy supply and non-supply. The duration for an optimal pulse-pause ratio depends on the thermal capacity of the heating element and can be between milliseconds and a few minutes.

In doing so, the heat to the individual heating and/or cooling devices 10 or heating and/or cooling patches can be controlled autonomously and intelligently among themselves. This means that each heating and/or cooling device 10 can control its own temperature or receive control commands. The heating and/or cooling device 10 can communicate or receive data from its sensors and/or its operating status, e.g. other heating and/or cooling devices 10. An intelligent distribution of heat can be generated by artificial intelligence. A selection of different heat therapy scenarios can thus be provided. Software and/or artificial intelligence can be used to expand and regulate the system as required.

Depending on the posture or incorrect posture, the energy or heat and/or cold can be distributed unequally or intelligently by the heating and/or cooling devices at a certain time, so that individual heating and/or cooling elements of the heating and/or cooling pad are simultaneously supplied with different amounts of energy. The energy can also be supplied in a time-variant manner such that heating and/or cooling elements are supplied with energy one after the other. As a result, pain can be relieved and tensions can be released. The signal processor can be designed such that it is able to detect a posture of the person based on the posture data and to control the delivery of the electric current to at least one of the heating and/or cooling elements. Body data can be generated by the at least one posture sensor. This body data can be transmitted to the signal processor. Depending on the body data, the signal processor can generate the control signal by means of which the energy output from the energy source to the heating and/or cooling element can be controlled.

FIG. 6 shows a system 30 for delivering heating and/or cooling energy to the body of a living being by means of different heating and/or cooling devices 10. The system 10 can comprise at least two heating and/or cooling devices 10 having a radio unit 36, the heating and/or cooling devices 10 being designed to send data and/or receive data. The heating and/or cooling devices 10 could also be connected by a cable, for example to one another and/or to a central energy source 22 and/or a signal processor 16. The heating and/or cooling devices 10 can also be connected to each other for data exchange, e.g. via a radio link 32. The data can be posture data, temperature data, data for controlling the energy source 22, signal processing data, sensor data, control data, operating data or any other data. The data can be sent from a first heating and/or cooling device 10 to a second heating and/or cooling device 10. The heating and/or cooling devices 10 can thus exchange data with one another to form a system 30 or a network 30. The connection can be carried out, for example, via a radio link 32, via a Piconet such as Bluetooth, RF24, RF32, ANT or NFC (near field communication). The heating and/or cooling devices 10 can also be connected to one another or to a central control or energy supply via electrical lines.

In general, heating and/or cooling devices 10 can have many different shapes, as shown in FIG. 6. In particular, the heating and/or cooling devices 10 may be round, oval, square or any other shape preferably adapted to the shape of the muscles to be stimulated.

Figure 7:
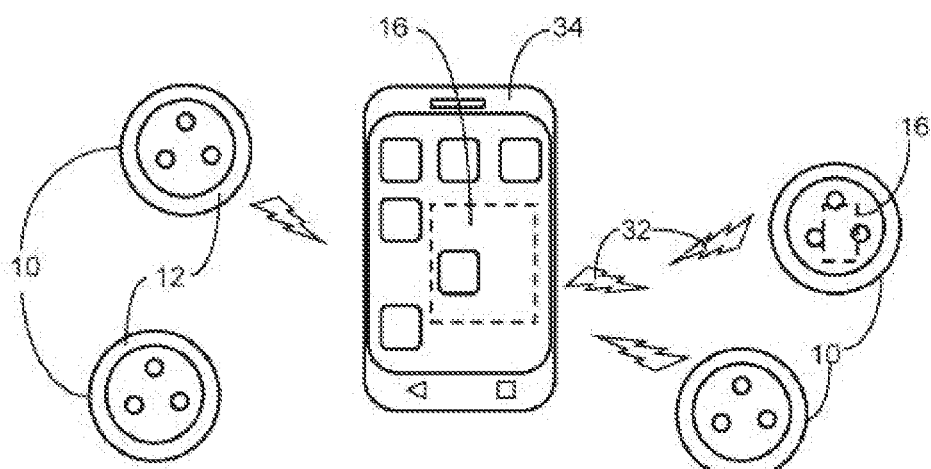
FIG. 7 shows a system for delivering heating and/or cooling energy to the body of a living being by means of a mobile device.

FIG. 7 shows a system 30 for delivering heating and/or cooling energy to the body 28 using a mobile device 34. The system 30 can comprise at least one first heating and/or cooling device 10, and at least one second heating and/or cooling device 10 and a mobile device 34. The first and second heating and/or cooling device 10 and the mobile device 34 are capable of exchanging data with each other. Each of the heating and/or cooling devices 10 shown can be designed to send data to a mobile device 34 and/or to receive data from a mobile device 34. The heating and/or cooling device 10 can be connected to a mobile telephone 34 for data exchange via the radio unit 36. The data may in turn be posture data, temperature data, data for controlling the energy source 22, signal processing data, sensor data, control data, operating data or any other data. The data can be sent from the heating and/or cooling device 10 to the mobile telephone 34 or to another heating and/or cooling device 10. The heating and/or cooling devices 10 can thus exchange data between the mobile telephone 34 or other heating and/or cooling devices 10 to form a system 30 or a network 30. The connection can be created, for example, via a radio link 32, via a Piconet such as Bluetooth, RF24, RF32, ANT or NFC (near field communication). Instead of a mobile telephone 34, it is also possible to use a smartphone or tablet or a mobile device specially designed for improving posture. The heating and/or cooling devices 10 can also be connected to the mobile device 34 or an energy supply via electrical lines, for example.

Using a mobile device such as a smartphone or tablet, data can be received, evaluated or displayed via a software application (app). The signal processor 16 can also be partly or completely located in the mobile device 34. The mobile device 34 can contain a signal processor 16, which receives the posture data via an interface of the mobile device 34, e.g. from the posture sensor. However, the mobile device 34 can also receive processed data from the signal processor 16 at an interface and, for example, display or store said data. The mobile device 34 can also receive at its interface, for example, posture data partially processed by the signal processor 16 and process said data additionally.

An app can be used to give the person tips for improving posture. The app can also be used to manually control individual heating and/or cooling devices 10 and supply them with energy or to mark regions on the body 28 which the person perceives as tense and wants to have supplied with heating and/or cooling energy to relax the regions. An intelligent, autonomous heating mode can also be set. A microcontroller-based and thus intelligent control 110 can supply or heat the warming and/or cooling pad 12 of the heating and/or cooling pad 10 with energy on the basis of stored data and algorithms. It is also possible for the user to define heat patterns, for example by drawing or changing lines in graphics. It is also possible to calibrate the system 30 first for existing incorrect posture, e.g. due to congenital deformation or illness. Deviations from this preexisting incorrect posture can then be detected and treated.

The app can also recommend to the person or user how to improve their posture, for example by showing them graphically or textually how to improve their posture. The app can also give the person or user suggestions for gymnastic exercises to improve posture, for example. The app can also provide the person with information from the Internet, which for example helps the person to improve posture. Furthermore, the app can also provide information regarding the person's false posture or suggestions for improvement to the person, for example by means of a film.

The improvement of the posture of the person can be achieved by consciously changing the posture of the person, e.g. by informing the person about poor posture by means of vibration or electrical impulses from a heating and/or cooling device 10 or by means of a display 101 on a mobile device 34. However, the improvement of the posture or the correction of the incorrect posture can also take place unconsciously for the person by relaxing individual muscles or muscle groups by supplying energy from the heating and/or cooling pad 10.

Figure 8A:
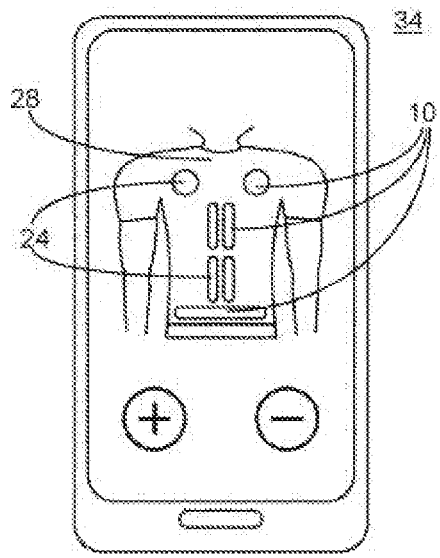
FIG. 8A-C show a mobile device with diagrams for improving posture.

In FIG. 8a, the outlines of the upper part of a body 28 of a living being are shown on a display 101 of a mobile device 34 such as a smartphone. The silhouette on the display 101 may show heating and/or cooling devices 10 and/or posture sensors 24 located on the body 28. The person who uses the system 30 to deliver the heating and/or cooling energy to the body 28 of a living being can be called a user. The user can, for example, enter, check or change the arrangement of the posture sensors 24 or the heating and/or cooling devices 10 on the body. It is also possible for the person 28 to influence or control the supply of electrical energy or the intensity with which thermal energy is delivered to the body 28 e.g. via the touch screen 101 of the mobile device 34. The influencing of the energy output is shown e.g. with a plus sign and a minus sign on the display 101 of the mobile device 34. By touching the plus sign the user can increase the energy output, for example. By touching the minus sign, the user can reduce the energy output, for example.

Figure 8B:
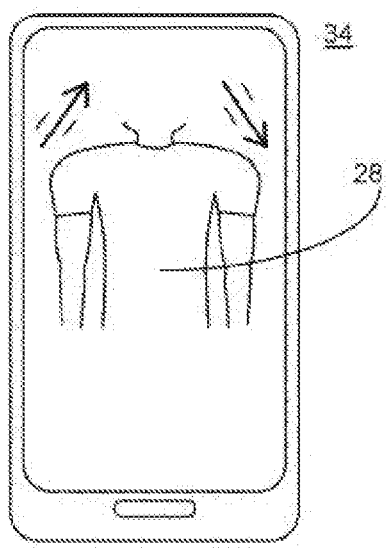

FIG. 8b shows the upper part of a body 28 of a living being on the display 101 of a mobile device 34 such as a smartphone. The display 101 can, for example, show the user their posture as detected by the system. The display 101 can also show the user how to improve their posture. The output of the suggestions for improvement can be supplemented with symbols or can be animated.

Figure 8C:
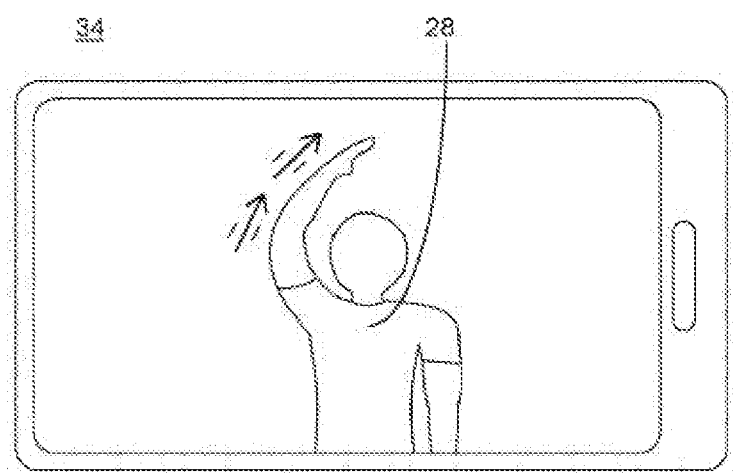

FIG. 8c again shows the upper part of a body 28 of a living being on the display 101 of a mobile device 34 such as a smartphone. As a mobile device 34, the smartphone can give suggestions to the user for improving the posture. The suggestions can include, for example, movement or gymnastics exercises that the user should perform. The suggestions can be sent to the user at a predefined time interval, so that the user is reminded or asked to perform movement or gymnastics exercises at a certain time once a day, for example. The exercises help the user, for example, to relax tense muscles or to strengthen muscles and thereby improve posture. The exercises can be described as active measures. The exercises can be personalized for a specific user or for a specific false posture, automatically compiled and output. The regular notification motivates more movement. This can counteract chronic tension and pain.

The combination of active and passive measures leads to a healthy and correct posture. Constant concentrated heat releases tensions so that the body can return to its natural posture. As a result, no long-term negative consequences arise.

In embodiments, the heating and/or cooling pad 12 can comprise an allergy-friendly or skin-friendly gel-like adhesive. This reduces the risk of an allergic reaction of the skin (allergy-friendly). Furthermore, the electrical energy source 22 can be rechargeable and can therefore be more sustainable than a conventional heat plaster. Since the heating and/or cooling pad 12 generates the heat by electrical energy and not, as with a heat plaster, by a chemical reaction, there is less risk of an allergic reaction to the chemical substances with the present heating and/or cooling device 10.

The heating and/or cooling device 10 can also be called a heat patch, heat pad, heating layer, heat plaster, heating mat or heating cushion. The heating and/or cooling device 10 may be intended for the localized, position-dependent delivery of thermal energy to the skin. The heating and/or cooling device 12 may also be referred to as a heating plaster or heating patch. The control unit can also be referred to as a control patch.

In embodiments, the heating and/or cooling device 10 can also be designed to deliver energy to the body in various forms. The delivery of different forms of energy to the body can be simultaneous or sequential. In a first phase, for example, thermal energy can be delivered to the body 28 of the person by the heating and/or cooling device 10. In a second phase, the same heating and/or cooling device 10 can, for example, release mechanical or electrical energy to the person's body. By stimulation with different forms of energy (mechanical, thermal, electrical), faster and more lasting relaxation of the muscle can be achieved.

Certain aspects have been described in connection with a device, but these aspects may also constitute a description of the corresponding method, so that a block or element of a device can also be understood as a corresponding method step or as a feature of a method step.

Accordingly, aspects described in connection with or as a method step also constitute a description of a corresponding block or detail or feature of a corresponding device. Some or all of the process steps may be carried out using hardware apparatus such as a smartphone, microcontroller, programmable computer or electronic circuit. In some examples, some or more of the main method steps may be carried out by such hardware.

Depending on implementation requirements, embodiments of the invention may be implemented in hardware or software. The implementation can be carried out using a digital storage medium, for example a memory stick, a memory card, a DVD, a Blu-ray disk, a CD, a ROM, a PROM, an EPROM, an EEPROM or a FLASH memory, a hard disk or any other magnetic or optical storage device on which electronically readable control signals are stored which can or do interact with a programmable computer system in such a way that the method in question is carried out. The digital storage medium may therefore be computer-readable.

Embodiments according to the invention may therefore include a data carrier which contains electronically readable control signals capable of interacting with a programmable computer system in such a way that one of the methods described herein can be carried out.

Embodiments of the present invention may be implemented as a computer program having a program code, the program code being able to carry out one of the methods when the computer program runs on a computer. The program code may, for example, also be stored on a machine-readable carrier.

Other embodiments comprise the computer program for carrying out one of the methods described herein, the computer program being stored on a machine-readable carrier.

An embodiment of the method according to the invention is thus, expressed differently, a computer program comprising a program code for carrying out one of the methods described herein when the computer program runs on a computer. The data carrier, digital storage medium or recorded medium is usually tangible or non-volatile.

Furthermore, another embodiment of the methods according to the invention is a data carrier (or a digital storage medium or a computer-readable medium) on which the computer program for carrying out one of the methods described herein is stored.

A further embodiment of the method according to the invention is a data stream or sequence of signals representing the computer program for carrying out one of the methods described herein. The data stream or sequence of signals may, for example, be configured to be transferred via a data communication link, for example via the Internet.

A further embodiment comprises a processing device, such as a computer, tablet, smartphone or programmable logic device, configured or adapted to carry out one of the methods described herein.

Another embodiment comprises a computer on which the computer program for carrying out one of the methods described herein is installed.

Another embodiment according to the invention comprises a device or system configured to transmit a computer program for carrying out at least one of the methods described herein to a receiver. The transmission may take place electronically or optically. The receiver may be, for example, a computer, mobile device, storage device, or similar device. For example, the device or system may comprise a file server for transferring the computer program to the recipient.

In embodiments, a programmable logic device (such as a field programmable gate array, FPGA) may be used to carry out some or all of the functions of the method described herein. In some embodiments, a field programmable gate array may interact with a microcontroller in order to carry out one of the methods described herein. In general, for some embodiments, the methods are carried out by any hardware device. This can be universally usable hardware such as a computer processor (CPU) or hardware specific to the method, such as an ASIC.

The embodiments described above are merely an illustration of the principles of the present invention. Modifications and alterations of the arrangements and details described herein may be obvious to other persons skilled in the art. Therefore, the invention shall be limited only by the scope of protection of the claims below and not by the specific details presented in the description and explanation of the embodiments herein.

LIST OF REFERENCE NUMERALS 10 heating and/or cooling device 10
12 heating and/or cooling pad
121 lower face of the heating and/or cooling pad
1210 adhesive surface
122 upper face of the heating and/or cooling pad
14 control unit
16 signal processor
18 electrical connector
18a electrical connecting element on the control unit
18b electrical connecting element on the heating and/or cooling pad
20 magnetic connector
20a mechanical and/or magnetic connecting element on the control unit
20b mechanical and/or magnetic connecting element on the heating and/or cooling pad
22 electrical energy source
24 posture sensor
241 bending sensor
26 heating or cooling element
28 body
30 system, network
32 radio link
34 mobile device
36 radio unit
38 temperature sensor
40 electrodes
42 vibration generator
101 display
102 antenna
104 charging circuit
107 skin detection sensor
108 analog/digital converter
109 safety monitoring and protection device
110 microcontroller
112 pulse width modulation power control
113 current, voltage, energy and/or power monitoring
114 further stimulants
116 further analog sensors and detectors
117 further digital sensors and detectors

The invention claimed is:

1. A heating and cooling device for delivering heating and cooling energy to the body, comprising:
a heating and cooling pad which can be connected to the body, which has an upper face and a lower face and on the lower face of which an adhesive surface is provided for fastening the heating and cooling pad to the surface of the skin of the body, and which comprises at least one heating and cooling element arranged to convert electrical energy emitted by an electrical energy source into heating and cooling energy;
a control unit which is provided to receive the energy source, which has a signal processor and which is provided to output an open-loop and/or closed-loop control signal arranged to control the energy output from the energy source to the heating and cooling element in an open-loop and/or closed-loop manner;
wherein the heating and cooling pad and the control unit can be electrically and mechanically connected to one another by at least one electrical connector, via which the electrical energy can be transmitted to the heating and cooling element, and at least one magnetic connector;
and wherein the heating and cooling pad has a square overall shape with rounded corners and a periphery,
and the overall shape has eight approximately-triangular heating elements having resistive heating conductors,
wherein each heating element extends from the center of the square overall shape as far as the periphery of the square overall shape of the heating pad,
and wherein each of the eight heating elements has two parts, specifically a portion at the center of the heating pad and a further portion at the periphery of the heating and cooling pad,
both the portion at the center and the portion at the periphery having the resistive heating conductors,
wherein the resistive heating conductors of the portions at the center of each of the eight heating elements are closer together to each other than the resistive heating conductors of the portions at the periphery of the respective heating element, and the portion at the center and the portion at the periphery of each of the heating elements are electrically connected to one another such that when a current is applied to each of the heating elements, the portions at the center heat up more quickly than the portions at the periphery.

2. The heating and cooling device according to claim 1, wherein the heating and cooling pad and the control unit can be electrically and mechanically connected to one another by:
a further electrical connector via which the electrical energy can be transmitted to the heating and cooling element, and
a further magnetic connector.

3. The heating and cooling device according to claim 1, wherein the electrical energy source and the heating and cooling element are designed to heat and/or cool the heating and cooling pad by 20 K in less than 1 minute, preferably in less than 20 seconds, particularly preferably in less than 5 seconds.

4. The heating and cooling device according to claim 1, wherein the heating and cooling device comprises at least one posture sensor and the posture sensor is designed to detect the posture and/or the movement of the body at least in part and to generate posture data arranged to control the energy output from the energy source to the heating and cooling element in an open-loop and/or closed-loop manner.

5. The heating and cooling device according to claim 1, wherein the heating and cooling device comprises a radio unit for transmitting and/or receiving data.

6. The heating and cooling device according to claim 1, the heating and cooling device comprising a temperature sensor which is designed to generate temperature data and the signal processor is designed to generate the open-loop and/or closed-loop control signal for open-loop and/or closed-loop control of the electrical energy source depending on the temperature data.

7. The heating and cooling device according to claim 1, wherein electrodes are arranged on the lower face of the heating and cooling pad and the signal processor is designed to determine the muscle tension by electromyography and/or the skin resistance by measuring the conductance.

8. The heating and cooling device according to claim 1, wherein the adhesive surface of the heating and cooling pad comprises an adhesive, preferably a pressure-sensitive adhesive.

9. The heating and cooling device according to claim 8, wherein the adhesive is gel-like.

10. The heating and cooling device according to claim 1, wherein the heating and cooling pad is a disposable element and the control unit is a reusable element.

11. The heating and cooling device according to claim 1, wherein the heating and cooling device comprises a vibration generator which is designed to convert electrical energy emitted by the electrical energy source into mechanical energy which can be transmitted to the body.

* * * * *